(12) United States Patent
Sun et al.

(10) Patent No.: US 9,717,706 B2
(45) Date of Patent: *Aug. 1, 2017

(54) CHROMONE INHIBITORS OF S-NITROSOGLUTATHIONE REDUCTASE

(71) Applicant: Nivalis Therapeutics, Inc., Boulder, CO (US)

(72) Inventors: Xicheng Sun, Broomfield, CO (US); Jian Qiu, Longmont, CO (US); Jan Wasley, Guilford, CT (US)

(73) Assignee: Nivalis Therapeutics, Inc., Boulder, CO (US)

(*) Notice: Subject to any disclaimer, the term of this patent is extended or adjusted under 35 U.S.C. 154(b) by 0 days.

This patent is subject to a terminal disclaimer.

(21) Appl. No.: 14/826,329

(22) Filed: Aug. 14, 2015

(65) Prior Publication Data

US 2015/0352073 A1 Dec. 10, 2015

Related U.S. Application Data

(60) Continuation of application No. 14/168,595, filed on Jan. 30, 2014, now abandoned, which is a continuation of application No. 13/912,287, filed on Jun. 7, 2013, now Pat. No. 8,669,381, which is a division of application No. 13/521,820, filed as application No. PCT/US2010/024035 on Feb. 12, 2010, now Pat. No. 8,481,590.

(51) Int. Cl.
| | | |
|---|---|---|
| A61K 31/352 | (2006.01) |
| A61K 31/381 | (2006.01) |
| C07D 311/34 | (2006.01) |
| C07D 311/36 | (2006.01) |
| C07D 409/04 | (2006.01) |

(52) U.S. Cl.
CPC .......... *A61K 31/352* (2013.01); *A61K 31/381* (2013.01); *C07D 311/34* (2013.01); *C07D 311/36* (2013.01); *C07D 409/04* (2013.01)

(58) Field of Classification Search
CPC .. A61K 31/352; A61K 31/381; C07D 409/04; C07D 311/34; C07D 311/36
See application file for complete search history.

(56) References Cited

U.S. PATENT DOCUMENTS

| | | | |
|---|---|---|---|
| 4,814,346 | A | 3/1989 | Albert et al. |
| 5,919,813 | A | 7/1999 | de Juan, Jr. |
| 8,481,590 | B2 | 7/2013 | Sun et al. |
| 8,669,381 | B2 | 3/2014 | Sun et al. |
| 8,759,548 | B2 | 6/2014 | Sun et al. |
| 9,187,447 | B2 | 11/2015 | Sun et al. |
| 2002/0128205 | A1 | 9/2002 | Stamler et al. |
| 2003/0181510 | A1 | 9/2003 | Baker et al. |
| 2004/0220180 | A1 | 11/2004 | Glick |
| 2005/0014697 | A1 | 1/2005 | Stamler et al. |
| 2005/0080024 | A1 | 4/2005 | Tucker et al. |
| 2005/0187166 | A1 | 8/2005 | Stamler et al. |
| 2005/0245603 | A1 | 11/2005 | Druzgala et al. |
| 2006/0247305 | A1 | 11/2006 | Wang et al. |
| 2006/0287388 | A1 | 12/2006 | Druzgala et al. |
| 2009/0029987 | A1 | 1/2009 | Wong et al. |
| 2010/0286174 | A1 | 11/2010 | Stamler et al. |
| 2012/0289555 | A1 | 11/2012 | Sun et al. |
| 2012/0295966 | A1 | 11/2012 | Sun et al. |
| 2013/0274320 | A1 | 10/2013 | Sun et al. |
| 2014/0094465 | A1 | 4/2014 | Sun et al. |
| 2014/0163092 | A1 | 6/2014 | Sun et al. |
| 2014/0275185 | A1 | 9/2014 | Sun et al. |
| 2016/0045478 | A1 | 2/2016 | Sun et al. |

FOREIGN PATENT DOCUMENTS

| | | |
|---|---|---|
| CN | 1475488 | 2/2004 |
| CN | 101365446 A | 2/2009 |
| EP | 2533637 | 3/2014 |
| WO | WO 97/31007 | 8/1997 |
| WO | WO 97/32872 | 9/1997 |
| WO | WO 00/10993 | 3/2000 |
| WO | WO 01/80855 | 11/2001 |
| WO | WO 02/055072 | 7/2002 |
| WO | WO 2004/002470 | 1/2004 |
| WO | WO 2004/037193 | 5/2004 |
| WO | WO 2006/099193 | 9/2006 |
| WO | WO 2007/016525 A2 | 2/2007 |
| WO | WO 2008/032105 | 3/2008 |
| WO | WO 2008/052256 | 5/2008 |
| WO | WO 2009/026657 | 3/2009 |
| WO | WO 2009/076665 | 6/2009 |
| WO | WO 2010/107476 | 9/2010 |
| WO | WO 2011/099978 | 8/2011 |
| WO | WO 2011/100433 | 8/2011 |

OTHER PUBLICATIONS

Alzhimer's Prevention (2014), http://www.webmd.com/alzheimers/tc/alzheimers-disease-prevention: p. 1-2.
Bouras, et al. (2010), Journal of visceral surgery 147.6 e351-e358. "Management of blunt hepatic trauma."
Chen et al. (2013) Journal of Applied Physiology 114:752-760, "Pharmacological inhibition of S-nitrosoglutathione reductase improves endothelial vasodilatory function in rats in vivo."
Cox, A., et al. (2014) Cell reports 6:56-69. "S-nitrosothiol signaling regulates liver development and improves outcome following toxic liver injury."
Cox, J. et al. (Jun. 2010) Comparative Medicine 60(3): 218-224, "Development and Characterization of a Rat Model of Nonpenetrating Liver Trauma".
de Belder et al. (May 1994) "Effects of S-nitroso-glutathione in the human forearm circulation; evidence for selective inhibition of platelet activation", *Cardiovasc Res.*, 28(5):691-694.
de Jesus-Berrios et al. (Nov. 2003) "Enzymes that Counteract Nitrosative Stress Promot Fungal Virulence", *Curr. Biol.*, 13:1963-1968.

(Continued)

Primary Examiner — Samantha Shterengarts
Assistant Examiner — Matt Mauro
(74) Attorney, Agent, or Firm — Swanson & Bratschun, L.L.C.

(57) ABSTRACT

The present invention is directed to inhibitors of S-nitrosoglutathione reductase (GSNOR), pharmaceutical compositions comprising such GSNOR inhibitors, and methods of making and using the same.

12 Claims, No Drawings

(56) References Cited

OTHER PUBLICATIONS

Ding et al. (2005) "Efficient Synthesis of Isolflavone Analogues via a Suzuki Coupling Reaction" *Tetrahedron Letters* 46:3707-3709.
EP Search Report issued in EP 10845917.3 on Jun. 14, 2013.
EP Search Report issued in EP 11742796.3 on May 8, 2013.
Foster et al. (Apr. 2003) "S-nitrosylation in health and disease", *Trends in Molecular Medicine*, 9(4):160-168.
Foster, et al. (2009), Trends in Molecular Medicine 15(9):391-404, "Protein S-nitrosylation in health and disease: a current perspective."
Galietta et al. (Jun. 8, 2001) "Novel CFTR Chloride Channel Activators Identified by Screening of Combinatorial Librariers Based on Flavone and Benzoquinolizinium Lead Compounds" *J. Biol. Chem.* 276 (23):19723-19728.
Gaston et al. (Dec. 1993) "Endogenous nitrogen oxides and bronchodilator S-nitorsolthiols in human airways", *Proc. Natl. Acad. Sci. USA*, 90:10957-10961.
International Preliminary Report on Patentability mailed on Aug. 23, 2012 in PCT/U52010/024035.
International Preliminary Report on Patentability mailed on Aug. 23, 2012 in PCT/US2011/024353.
International Search Report and Written Opinion mailed Apr. 14, 2011 in PCT/US2011/024353.
International Search Report and Written Opinion mailed Apr. 2, 2010 in PCT/U52010/024035.
Jensen et al. (1998) "S-Nitrosoglutathione is a substrate for rat alcohol dehydrognease class III isoenzyme", *Biochem J.*, 331:659-668.
Kaposzta et al. (2002) "S-Nitrosoglutathione Reduces Asymptomatic Embolization After Carotid Angioplasty", *Circulation*,106(24):3057-3062.
Keri et al.(2014). European Journal of Medicinal Chemistry 78:340-374, "Chromones as a privileged scaffold in drug discovery: A Review."
Lipton et al. (Sep. 2001) "S-Nitrosothiols signal the ventilatory response to hypoxia", *Nature*, 413:171-174.
Liu et al. (Feb. 2004) "Essential Roles of S-Nitrosothiols in Vascular Homeostatsis and Endotoxic Shock", *Cell*, 116(4):617-628.
Liu et al. (Mar. 2001) "A metabolic enzyme for S-nitrosothiol conserved from bacterial to humans", *Nature*, 410:490-494.
Matin et al., (2009) "7-Hydroxy-benzopyran-4-one Derivatives: A Novel Pharmocophone of Peroxisome Proliferator-Activated Receptor α- and γ-(PPARα and γ) Dual Agonists" *J. Med. Chem.* ,52:6835-6850.

Patani et al. (1996) Che. Rev. 96:3147-3176, "Bioisosterism: A Rational Approach in Drug Design".
Que et al. (Jun. 2005) "Protection from Experimental Asthma by an Endogenous Bronchodilator", *Science*, 308(5728):1618-1621.
Rheumatoid Arthritis Prevention (2014) http://www.webmd.com/rheumatoid-arthritis/rheumatoid-arthritis-prevention: p. 1-2.
Sanghani et al. (2000) "Kinetic Mechanism of Human Glutathioone-Dependent Formaldehyde Dehydrogenase", *Biochemistry*,39:10720-10729.
Sanghani et al. (2002) "Human Glutathione-Dependent Formaldehyde Dehydrognease. Structures of Apo, Binary, and Inhibitory Ternary Complexes", *Biochemistry*,41:10778-10786.
Savidge, T.C., (2014) Current Opinion in Pharmacology 19:54-60. "Importance of NO and its related compounds in enteric nervous system regulation of gut homeostasis and disease susceptibility."
Scifinder search results for 4-[7-hydroxy-4-oxo-2-(trifluoromethyl)-4-H-chromen-3 yl] benzoic acid with the catalogue listings, Dec. 2009.
Sepulveda-Boza et al. (2001) "The Preparations of New Isoflavones" *Synthetic Communications*, 31(12):1933-1940.
Staab et al. (2008) "Dual functions of alcohol dehydrogenase 3: implications with focus on formaldehyde dehydrogenase and S-nitroglutathione reductase activities" *Cell Mol. Life Sci*, 65:3950-3960.
Staab et al. (Jun. 15, 2009) "Medium-chain fatty acids and glutathione derivatives as inhibitors of S-nitrosoglutathione reduction mediated by alcohol dehydrogenase 3", Chemico-Biological Interactions 180(1):113-118.
Stamler et al. (Aug. 1992) "Nitric oxide circulates in mammalian plasma primarily as an S-nitrose adduct of serium albumin", *Proc. Natl. Acad. Sci. USA*, 89:7674-7677.
Sun et al. (2011) ACS medicinal chemistry letters 2:402-406. "Discovery of S-nitrosoglutathione reductase inhibitors: potential agents for the treatment of asthma and other inflammatory diseases."
Tang, et al. (2013 : Cancer research 73:2897-2904. "Hepatocarcinogenesis driven By GSNOR deficiency is prevented by iNOS inhibition."
Uotila and Koivusalo (1989) Coenzymes and Cofactors vol. 3: Glutathione, part A., D. Dolphin, ed. pp. 517-551 (New York, John Wiley & Sons).
Wang, et al. Experimental and Toxicologic Pathology (2014) 66: 351-356. "Molecular mechanisms of liver injury: Apoptosis or necrosis."
Zaman et al. (2001) "S-Nitrosoglutathione Increases Cystic Fibrosis Transmembrane Regulator Maturation", *Biochem Biophys Res Commun.*, 284:65-70.

CHROMONE INHIBITORS OF S-NITROSOGLUTATHIONE REDUCTASE

CROSS-REFERENCE TO RELATED APPLICATIONS

This application is a continuation of U.S. application Ser. No. 14/168,595, filed Jan. 30, 2014. U.S. application Ser. No. 14/168,595 is a continuation of U.S. application Ser. No. 13/912,287, filed Jun. 7, 2013, now U.S. Pat. No. 8,669,381. U.S. application Ser. No. 13/912,287 is a divisional of U.S. application Ser. No. 13/521,820, filed Jul. 12, 2012, now U.S. Pat. No. 8,481,590, issued Jul. 9, 2013. U.S. application Ser. No. 13/521,820 is a 35 U.S.C. §371 national phase application of PCT/US2010/024035, filed Feb. 12, 2010 (WO 2011/099978). Each of the referenced applications is incorporated herein by reference in its entirety.

FIELD OF THE INVENTION

The present invention is directed to novel chromone inhibitors of S-nitrosoglutathione reductase, pharmaceutical compositions comprising such inhibitors, and methods of making and using the same.

BACKGROUND OF THE INVENTION

The chemical compound nitric oxide is a gas with the chemical formula NO. NO is one of the few gaseous signaling molecules known in biological systems, and plays an important role in controlling various biological events. For example, the endothelium uses NO to signal surrounding smooth muscle in the walls of arterioles to relax, resulting in vasodilation and increased blood flow to hypoxic tissues. NO is also involved in regulating smooth muscle proliferation, platelet function, neurotransmission, and plays a role in host defense. Although nitric oxide is highly reactive and has a lifetime of a few seconds, it can both diffuse freely across membranes and bind to many molecular targets. These attributes make NO an ideal signaling molecule capable of controlling biological events between adjacent cells and within cells.

NO is a free radical gas, which makes it reactive and unstable, thus NO is short lived in vivo, having a half life of 3-5 seconds under physiologic conditions. In the presence of oxygen, NO can combine with thiols to generate a biologically important class of stable NO adducts called S-nitrosothiols (SNO's). This stable pool of NO has been postulated to act as a source of bioactive NO and as such appears to be critically important in health and disease, given the centrality of NO in cellular homeostasis (Stamler et al., *Proc. Natl. Acad. Sci. USA*, 89:7674-7677 (1992)). Protein SNO's play broad roles in cardiovascular, respiratory, metabolic, gastrointestinal, immune and central nervous system function (Foster et al., 2003, Trends in Molecular Medicine Volume 9, Issue 4, April 2003, pages 160-168). One of the most studied SNO's in biological systems is S-nitrosoglutathione (GSNO) (Gaston et al., *Proc. Natl. Acad. Sci. USA* 90:10957-10961 (1993)), an emerging key regulator in NO signaling since it is an efficient trans-nitrosating agent and appears to maintain an equilibrium with other S-nitrosated proteins (Liu et al., 2001) within cells. Given this pivotal position in the NO—SNO continuum, GSNO provides a therapeutically promising target to consider when NO modulation is pharmacologically warranted.

In light of this understanding of GSNO as a key regulator of NO homeostasis and cellular SNO levels, studies have focused on examining endogenous production of GSNO and SNO proteins, which occurs downstream from the production of the NO radical by the nitric oxide synthetase (NOS) enzymes. More recently there has been an increasing understanding of enzymatic catabolism of GSNO which has an important role in governing available concentrations of GSNO and consequently available NO and SNO's.

Central to this understanding of GSNO catabolism, researchers have recently identified a highly conserved S-nitrosoglutathione reductase (GSNOR) (Jensen et al., *Biochem J.*, 331:659-668 (1998); Liu et al., *Nature,* 410:490-494 (2001)). GSNOR is also known as glutathione-dependent formaldehyde dehydrogenase (GS-FDH), alcohol dehydrogenase 3 (ADH class 3) (Uotila and Koivusalo, *Coenzymes and Cofactors.*, D. Dolphin, ed. pp. 517-551 (New York, John Wiley & Sons, 1989)), and alcohol dehydrogenase 5 (ADH5) Importantly GSNOR shows greater activity toward GSNO than other substrates (Jensen et al., 1998; Liu et al., 2001) and appears to mediate important protein and peptide denitrosating activity in bacteria, plants, and animals. GSNOR appears to be the major GSNO-metabolizing enzyme in eukaryotes (Liu et al., 2001). Thus, GSNO can accumulate in biological compartments where GSNOR activity is low or absent (e.g. airway lining fluid) (Gaston et al., 1993).

Yeast deficient in GSNOR accumulate S-nitrosylated proteins which are not substrates of the enzyme, which is strongly suggestive that GSNO exists in equilibrium with SNO-proteins (Liu et al., 2001). Precise enzymatic control over ambient levels of GSNO and thus SNO-proteins raises the possibility that GSNO/GSNOR may play roles across a host of physiological and pathological functions including protection against nitrosative stress wherein NO is produced in excess of physiologic needs. Indeed, GSNO specifically has been implicated in physiologic processes ranging from the drive to breathe (Lipton et al., *Nature,* 413:171-174 (2001)) to regulation of the cystic fibrosis transmembrane regulator (Zaman et al., *Biochem Biophys Res Commun,* 284:65-70 (2001), to regulation of vascular tone, thrombosis and platelet function (de Belder et al., Cardiovasc Res. 1994 May; 28(5):691-4. (1994); Z. Kaposzta, A et al., Circulation; 106(24): 3057-3062, 2002) as well as host defense (de Jesus-Berrios et al., *Curr. Biol.,* 13:1963-1968 (2003)). Other studies have found that GSNOR protects yeast cells against nitrosative stress both in vitro (Liu et al., 2001) and in vivo (de Jesus-Berrios et al., 2003).

Collectively data suggest GSNO as a primary physiological ligand for the enzyme S-nitrosoglutathione reductase (GSNOR), which catabolizes GSNO and consequently reduces available SNO's and NO in biological systems (Liu et al., 2001), (Liu et al., Cell, (2004), 116(4), 617-628), and (Que et al., Science, 2005, 308, (5728):1618-1621). As such, this enzyme plays a central role in regulating local and systemic bioactive NO. Since perturbations in NO bioavailability has been linked to the pathogenesis of numerous disease states, including hypertension, atherosclerosis, thrombosis, asthma, gastrointestinal disorders, inflammation and cancer, agents that regulate GSNOR activity are candidate therapeutic agents for treating diseases associated with nitric oxide imbalance.

Currently, there is a great need in the art for diagnostics, prophylaxis, ameliorations, and treatments for medical conditions relating to increased NO synthesis and/or increased NO bioactivity. In addition, there is a significant need for novel compounds, compositions and methods for preventing, ameliorating, or reversing other NO-associated disorders. The present invention satisfies these needs.

SUMMARY OF THE INVENTION

The present invention provides novel chromone compounds useful as S-nitrosoglutathione reductase ("GSNOR") inhibitors. The invention encompasses pharmaceutically acceptable salts, prodrugs, and metabolites of the described GSNOR inhibitors. Also encompassed by the invention are pharmaceutical compositions comprising at least one GSNOR inhibitor and at least one pharmaceutically acceptable carrier.

The compositions of the present invention can be prepared in any suitable pharmaceutically acceptable dosage form.

The present invention provides a method for inhibiting S-nitrosoglutathione reductase in a subject in need thereof. Such a method comprises administering a therapeutically effective amount of a pharmaceutical composition comprising at least one GSNOR inhibitor or a pharmaceutically acceptable salt thereof, a prodrug or metabolite thereof, in combination with at least one pharmaceutically acceptable carrier. The GSNOR inhibitor can be a novel compound according to the invention, or it can be a known compound which previously was not known to be an inhibitor of GSNOR.

The present invention also provides a method of treating a disorder ameliorated by NO donor therapy in a subject in need thereof. Such a method comprises administering a therapeutically effective amount of a pharmaceutical composition comprising at least one GSNOR inhibitor or a pharmaceutically acceptable salt thereof, a prodrug, or metabolite thereof, in combination with at least one pharmaceutically acceptable carrier. The GSNOR inhibitor can be a novel compound according to the invention, or it can be a known compound which previously was not known to be an inhibitor of GSNOR.

The present invention also provides a method of treating a cell proliferative disorder in a subject in need thereof. Such a method comprises administering a therapeutically effective amount of a pharmaceutical composition comprising at least one GSNOR inhibitor or a pharmaceutically acceptable salt thereof, a prodrug, or metabolite thereof, in combination with at least one pharmaceutically acceptable carrier. The GSNOR inhibitor can be a novel compound according to the invention, or it can be a known compound which previously was not known to be an inhibitor of GSNOR.

The methods of the invention encompass administration with one or more secondary active agents. Such administration can be sequential or in a combination composition.

Although methods and materials similar or equivalent to those described herein can be used in the practice or testing of the present invention, suitable methods and materials are described below. All publicly available publications, patent applications, patents, and other references mentioned herein are incorporated by reference in their entirety. In the case of conflict, the present specification, including definitions, will control.

Both the foregoing summary and the following detailed description are exemplary and explanatory and are intended to provide further details of the compositions and methods as claimed. Other objects, advantages, and novel features will be readily apparent to those skilled in the art from the following detailed description.

DETAILED DESCRIPTION OF THE PREFERRED EMBODIMENTS

A. Overview of the Invention

Until recently, S-nitrosoglutathione reductase (GSNOR) was known to oxidize the formaldehyde glutathione adduct, S-hydroxymethylglutathione. GSNOR has since been identified in a variety of bacteria, yeasts, plants and animals and is well conserved. The proteins from *E. coli*, *S. cerevisiae* and mouse macrophages share over 60% amino acid sequence identity. GSNOR activity (i.e., decomposition of S-nitrosoglutathione when NADH is present as a required cofactor) has been detected in *E. coli*, in mouse macrophages, in mouse endothelial cells, in mouse smooth muscle cells, in yeasts, and in human HeLa, epithelial and monocyte cells. Human GSNOR nucleotide and amino acid sequence information can be obtained from the National Center for Biotechnology Information (NCBI) databases under Accession Nos. M29872, NM_000671. Mouse GSNOR nucleotide and amino acid sequence information can be obtained from NCBI databases under Accession Nos. NM_007410. In the nucleotide sequence, the start site and stop site are underlined. CDS designates coding sequence. SNP designates single nucleotide polymorphism. Other related GSNOR nucleotide and amino acid sequences, including those of other species, can be found in U.S. Patent Application 2005/0014697.

In accord with the present invention, GSNOR has been shown to function in vivo and in vitro to metabolize S-nitrosoglutathione (GSNO) and protein S-nitrosothiols (SNOs) to modulate NO bioactivity, by controlling the intracellular levels of low mass NO donor compounds and preventing protein nitrosylation from reaching toxic levels.

Based on this, it follows that inhibition of this enzyme potentiates bioactivity in all diseases in which NO donor therapy is indicated, inhibits the proliferation of pathologically proliferating cells, and increases NO bioactivity in diseases where this is beneficial.

B. S-Nitrosoglutathione Reductase Inhibitors

1. Inventive Compounds

The present invention provides pharmaceutical agents that are potent inhibitors of GSNOR. In particular, provided are substituted chromone analogs that are inhibitors of GSNOR having the structure depicted below (Formula I), or a pharmaceutically acceptable salt, stereoisomer, or prodrug thereof.

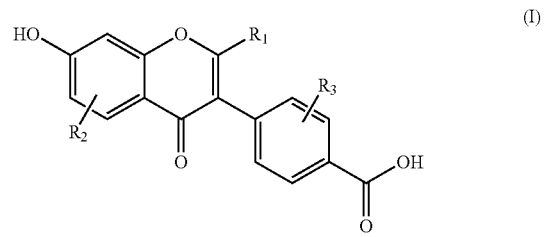

(I)

wherein
$R_1$ is selected from the group consisting of $CF_3$, $CF_2H$, $CF_2CH_3$, $CF_2CH_2CH_3$, methyl, isopropyl, isobutyl, cyclopentyl, $CH_2OCH_3$, $SCH_3$, benzyl, thiophen-2-yl, and thiophen-3-yl;
$R_2$ is selected from H, F, Cl, methoxy, and cyano; and
$R_3$ is selected from H, F, Cl, and methoxy.

In a further aspect of the invention, $R_1$ is selected from $CF_3$, $CF_2H$, and $CF_2CH_3$; and $R_2$ is hydrogen.

In a further aspect of the invention, $R_1$ is selected from the group consisting of $CF_3$, methyl, isopropyl, and isobutyl; and $R_2$ and $R_3$ are both hydrogen.

In yet another aspect of the invention, $R_1$ is selected from the group consisting of $CF_3$, methyl, isopropyl, isobutyl, $CF_2H$, $CF_2CH_3$, and $CF_2CH_2CH_3$; and $R_2$ and $R_3$ are both hydrogen.

In a further aspect of the invention, suitable compounds of Formula I include, but are not limited to:

4-(2-(difluoromethyl)-7-hydroxy-4-oxo-4H-chromen-3-yl) benzoic acid;
4-(7-hydroxy-2-(methoxymethyl)-4-oxo-4H-chromen-3-yl) benzoic acid;
4-(7-hydroxy-2-isopropyl-4-oxo-4H-chromen-3-yl)benzoic acid;
4-(2-cyclopentyl-7-hydroxy-4-oxo-4H-chromen-3-yl)benzoic acid;
4-(7-hydroxy-2-methyl-4-oxo-4H-chromen-3-yl)benzoic acid;
4-(2-benzyl-7-hydroxy-4-oxo-4H-chromen-3-yl)benzoic acid;
4-(7-hydroxy-4-oxo-2-(thiophen-2-yl)-4H-chromen-3-yl) benzoic acid;
4-(7-hydroxy-4-oxo-2-(thiophen-3-yl)-4H-chromen-3-yl) benzoic acid;
4-(7-hydroxy-2-isobutyl-4-oxo-4H-chromen-3-yl)benzoic acid;
4-(7-hydroxy-4-oxo-2-(trifluoromethyl)-4H-chromen-3-yl) benzoic acid;
4-(7-hydroxy-2-(methylthio)-4-oxo-4H-chromen-3-yl)benzoic acid;
4-(6-chloro-7-hydroxy-4-oxo-2-(trifluoromethyl)-4H-chromen-3-yl)benzoic acid;
4-(6-fluoro-7-hydroxy-4-oxo-2-(trifluoromethyl)-4H-chromen-3-yl)benzoic acid;
2-fluoro-4-(7-hydroxy-4-oxo-2-(trifluoromethyl)-4H-chromen-3-yl)benzoic acid;
3-chloro-4-(7-hydroxy-4-oxo-2-(trifluoromethyl)-4H-chromen-3-yl)benzoic acid;
4-(2-(1,1-difluoroethyl)-7-hydroxy-4-oxo-4H-chromen-3-yl)benzoic acid;
4-(7-hydroxy-6-methoxy-4-oxo-2-(trifluoromethyl)-4H-chromen-3-yl)benzoic acid;
2-chloro-4-(7-hydroxy-4-oxo-2-(trifluoromethyl)-4H-chromen-3-yl)benzoic acid;
4-(2-(1,1-difluoropropyl)-7-hydroxy-4-oxo-4H-chromen-3-yl)benzoic acid;
4-(7-hydroxy-4-oxo-2-(trifluoromethyl)-4H-chromen-3-yl)-3-methoxybenzoic acid; and
4-(6-cyano-7-hydroxy-4-oxo-2-(trifluoromethyl)-4H-chromen-3-yl)benzoic acid.

Further, in any of the compositions described herein, one or more compounds or subgenus of compounds can be specifically excluded. In one embodiment of the invention, 4-(7-hydroxy-4-oxo-2-(trifluoromethyl)-4H-chromen-3-yl) benzoic acid is specifically excluded.

Substituted chromone analogs are potent inhibitors of GSNOR. As used in this context, the term "analog" refers to a compound having similar chemical structure and function as compounds of Formula I that retains the chromone core.

When a bond to a substituent is shown to cross a bond connecting two atoms in a ring, then such substituent may be bonded to any atom in the ring. When a substituent is listed without indicating the atom via which such substituent is bonded to the rest of the compound of a given formula, then such substituent may be bonded via any atom in such substituent. Combinations of substituents and/or variables are permissible, but only if such combinations result in stable compounds.

Some chromone analogs of the invention can also exist in various isomeric forms, including configurational, geometric and conformational isomers, as well as existing in various tautomeric forms, particularly those that differ in the point of attachment of a hydrogen atom. As used herein, the term "isomer" is intended to encompass all isomeric forms of a compound including tautomeric forms of the compound. All tautomers of shown or described compounds are also considered to be part of the present invention. Cis and trans geometric isomers of the compounds of the present invention are described and may be isolated as a mixture of isomers or as separated isomeric forms. Many geometric isomers of olefins, C=N double bonds, and the like can also be present in the compounds described herein, and all such stable isomers are contemplated in the present invention. All chiral, diastereomeric, racemic, and geometric isomeric forms of a structure are intended, unless the specific stereochemistry or isomeric form is specifically indicated.

The compounds described herein may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials.

It is to be understood that isomers arising from such asymmetry (e.g., all enantiomers and diastereomers) are included within the scope of the invention, unless indicated otherwise. Such isomers can be obtained in substantially pure form by classical separation techniques and by stereochemically controlled synthesis. Furthermore, the structures and other compounds and moieties discussed in this application also include all tautomers thereof. Alkenes can include either the E- or Z-geometry, where appropriate.

It should be noted that if there is a discrepancy between a depicted structure and a name given to that structure, the depicted structure controls. In addition, if the stereochemistry of a structure or a portion of a structure is not indicated with, for example, bold, wedged, or dashed lines, the structure or portion of the structure is to be interpreted as encompassing all stereoisomers of the described compound.

2. Representative GSNOR Inhibitors

Examples 1-21 list representative novel chromone analogs of Formula I. The synthetic methods that can be used to prepare each compound are detailed in Examples 1-21, with reference to the synthetic scheme depicted before Example 1, and reference to intermediates described in Example 23. Supporting mass spectrometry data and proton NMR data for each compound is also included in Examples 1-21. GSNOR inhibitor activity was determined by the assay described in Example 24 and $IC_{50}$ values were obtained. GSNOR inhibitor compounds Examples 1-21 had an $IC_{50}$ of about <5 µM. GSNOR inhibitor compounds Examples 1, 2, 3, 5, 6, 10, 13, 14, 15, 16, 18, 19, 20 had an $IC_{50}$ of about <0.5 µM. GSNOR inhibitor compounds Examples 1, 10, 14, 15, 16, 18, and 20 had an $IC_{50}$ of about <0.1 µM.

C. Definitions

As used herein, "about" will be understood by persons of ordinary skill in the art and will vary to some extent on the context in which it is used. If there are uses of the term which are not clear to persons of ordinary skill in the art given the context in which it is used, "about" will mean up to plus or minus 10% of the particular term.

As used herein, the term "bioactivity" indicates an effect on one or more cellular or extracellular process (e.g., via binding, signaling, etc.) which can impact physiological or pathophysiological processes.

As used herein and unless otherwise indicated, the term "stereoisomer" means one stereoisomer of a compound that is substantially free of other stereoisomers of that compound. For example, a stereomerically pure compound having one chiral center will be substantially free of the opposite enantiomer of the compound. A stereomerically pure compound having two chiral centers will be substantially free of other diastereomers of the compound. In some embodiments, a stereomerically pure compound comprises greater than about 80% by weight of one stereoisomer of the compound and less than about 20% by weight of other stereoisomers of the compound, for example greater than about 90% by weight of one stereoisomer of the compound and less than about 10% by weight of the other stereoisomers of the compound, or greater than about 95% by weight of one stereoisomer of the compound and less than about 5% by weight of the other stereoisomers of the compound, or greater than about 97% by weight of one stereoisomer of the compound and less than about 3% by weight of the other stereoisomers of the compound.

As used herein, "protein" is used synonymously with "peptide," "polypeptide," or "peptide fragment." A "purified" polypeptide, protein, peptide, or peptide fragment is substantially free of cellular material or other contaminating proteins from the cell, tissue, or cell-free source from which the amino acid sequence is obtained, or substantially free from chemical precursors or other chemicals when chemically synthesized.

As used herein, "modulate" is meant to refer to an increase or decrease the levels of a peptide or polypeptide, or to increase or decrease the stability or activity of a peptide or a polypeptide. The term "inhibit" is meant to refer to a decrease in the levels of a peptide or a polypeptide or to decrease in the stability or activity of a peptide or a polypeptide. In preferred embodiments, the peptide which is modulated or inhibited is S-nitrosoglutathione (GSNO) or protein S-nitrosothiols (SNOs).

As used here, the terms "nitric oxide" and "NO" encompass uncharged nitric oxide and charged nitric oxide species, particularly including nitrosonium ion (NO+) and nitroxyl ion (NO$^-$). The reactive form of nitric oxide can be provided by gaseous nitric oxide. Compounds having the structure X—NO$_y$, wherein X is a nitric oxide releasing, delivering or transferring moiety, including any and all such compounds which provide nitric oxide to its intended site of action in a form active for their intended purpose, and Y is 1 or 2.

As utilized herein, the term "pharmaceutically acceptable" means approved by a regulatory agency of a federal or a state government or listed in the U.S. Pharmacopoeia or other generally recognized pharmacopoeia for use in animals and, more particularly, in humans. The term "carrier" refers to a diluent, adjuvant, excipient, or vehicle with which the therapeutic is administered and includes, but is not limited to such sterile liquids as water and oils.

A "pharmaceutically acceptable salt" or "salt" of a GSNOR inhibitor is a product of the disclosed compound that contains an ionic bond, and is typically produced by reacting the disclosed compound with either an acid or a base, suitable for administering to a subject. A pharmaceutically acceptable salt can include, but is not limited to, acid addition salts including hydrochlorides, hydrobromides, phosphates, sulphates, hydrogen sulphates, alkylsulphonates, arylsulphonates, arylalkylsulfonates, acetates, benzoates, citrates, maleates, fumarates, succinates, lactates, and tartrates; alkali metal cations such as Li, Na, K, alkali earth metal salts such as Mg or Ca, or organic amine salts.

A "pharmaceutical composition" is a formulation comprising the disclosed compounds in a form suitable for administration to a subject. A pharmaceutical composition of the invention is preferably formulated to be compatible with its intended route of administration. Examples of routes of administration include, but are not limited to, oral and parenteral, e.g., intravenous, intradermal, subcutaneous, inhalation, topical, transdermal, transmucosal, and rectal administration.

"Stable compound" and "stable structure" are meant to indicate a compound that is sufficiently robust to survive isolation to a useful degree of purity from a reaction mixture, and formulation into an efficacious therapeutic agent.

As used herein the term "therapeutically effective amount" generally means the amount necessary to ameliorate at least one symptom of a disorder to be prevented, reduced, or treated as described herein. The phrase "therapeutically effective amount" as it relates to the GSNOR inhibitors of the present invention shall mean the GSNOR inhibitor dosage that provides the specific pharmacological response for which the GSNOR inhibitor is administered in a significant number of subjects in need of such treatment. It is emphasized that a therapeutically effective amount of a GSNOR inhibitor that is administered to a particular subject in a particular instance will not always be effective in treating the conditions/diseases described herein, even though such dosage is deemed to be a therapeutically effective amount by those of skill in the art.

The term "biological sample" includes, but is not limited to, samples of blood (e.g., serum, plasma, or whole blood), urine, saliva, sweat, breast milk, vaginal secretions, semen, hair follicles, skin, teeth, bones, nails, or other secretions, body fluids, tissues, or cells. In accordance with the invention, the levels of the S-nitrosoglutathione reductase in the biological sample can be determined by the methods described in U.S. Patent Application Publication No. 2005/0014697.

D. Pharmaceutical Compositions Comprising a GSNOR Inhibitor

The invention encompasses pharmaceutical compositions comprising at least one GSNOR inhibitor described herein and at least one pharmaceutically acceptable carrier. Suitable carriers are described in "Remington: The Science and Practice, Twentieth Edition," published by Lippincott Williams & Wilkins, which is incorporated herein by reference. Pharmaceutical compositions according to the invention may also comprise one or more non-GSNOR inhibitor active agents.

The pharmaceutical compositions of the invention can comprise novel GSNOR inhibitors described herein, the pharmaceutical compositions can comprise known compounds which previously were not know to have GSNOR inhibitor activity, or a combination thereof.

The GSNOR inhibitors can be utilized in any pharmaceutically acceptable dosage form, including but not limited to injectable dosage forms, liquid dispersions, gels, aerosols, ointments, creams, lyophilized formulations, dry powders, tablets, capsules, controlled release formulations, fast melt formulations, delayed release formulations, extended release formulations, pulsatile release formulations, mixed immediate release and controlled release formulations, etc. Specifically, the GSNOR inhibitors described herein can be formulated: (a) for administration selected from the group consisting of oral, pulmonary, intravenous, intra-arterial, intrathecal, intra-articular, rectal, ophthalmic, colonic, parenteral, intracisternal, intravaginal, intraperitoneal, local, buccal, nasal, and topical administration; (b) into a dosage form selected from the group consisting of liquid dispersions, gels, aerosols, ointments, creams, tablets, sachets and capsules; (c) into a dosage form selected from the group consisting of lyophilized formulations, dry powders, fast melt formulations, controlled release formulations, delayed release formulations, extended release formulations, pulsatile release formulations, and mixed immediate release and controlled release formulations; or (d) any combination thereof.

For respiratory infections, an inhalation formulation can be used to achieve high local concentrations. Formulations suitable for inhalation include dry power or aerosolized or vaporized solutions, dispersions, or suspensions capable of being dispensed by an inhaler or nebulizer into the endobronchial or nasal cavity of infected patients to treat upper and lower respiratory bacterial infections.

Solutions or suspensions used for parenteral, intradermal, or subcutaneous application can comprise one or more of the following components: (1) a sterile diluent such as water for injection, saline solution, fixed oils, polyethylene glycols, glycerine, propylene glycol or other synthetic solvents; (2) antibacterial agents such as benzyl alcohol or methyl parabens; (3) antioxidants such as ascorbic acid or sodium bisulfite; (4) chelating agents such as ethylenediaminetetraacetic acid; (5) buffers such as acetates, citrates or phosphates; and (5) agents for the adjustment of tonicity such as sodium chloride or dextrose. The pH can be adjusted with acids or bases, such as hydrochloric acid or sodium hydroxide. A parenteral preparation can be enclosed in ampoules, disposable syringes or multiple dose vials made of glass or plastic.

Pharmaceutical compositions suitable for injectable use may comprise sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL (BASF, Parsippany, N.J.) or phosphate buffered saline (PBS). In all cases, the composition must be sterile and should be fluid to the extent that easy syringability exists. The pharmaceutical composition should be stable under the conditions of manufacture and storage and should be preserved against the contaminating action of microorganisms such as bacteria and fungi.

The carrier can be a solvent or dispersion medium comprising, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol or sorbitol, and inorganic salts such as sodium chloride in the composition. Prolonged absorption of the injectable compositions can be brought about by including in the composition an agent which delays absorption, for example, aluminum monostearate and gelatin.

Sterile injectable solutions can be prepared by incorporating the active reagent (e.g., GSNOR inhibitor) in the required amount in an appropriate solvent with one or a combination of ingredients enumerated above, as required, followed by filtered sterilization. Generally, dispersions are prepared by incorporating at least one GSNOR inhibitor into a sterile vehicle that contains a basic dispersion medium and any other required ingredients. In the case of sterile powders for the preparation of sterile injectable solutions, exemplary methods of preparation include vacuum drying and freeze-drying, both of which yield a powder of the GSNOR inhibitor plus any additional desired ingredient from a previously sterile-filtered solution thereof.

Oral compositions generally include an inert diluent or an edible carrier. They can be enclosed, for example, in gelatin capsules or compressed into tablets. For the purpose of oral therapeutic administration, the GSNOR inhibitor can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition.

For administration by inhalation, the compounds are delivered in the form of an aerosol spray from pressured container or dispenser that contains a suitable propellant, e.g., a gas such as carbon dioxide, a nebulized liquid, or a dry powder from a suitable device. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active reagents are formulated into ointments, salves, gels, or creams as generally known in the art. The reagents can also be prepared in the form of suppositories (e.g., with conventional suppository bases such as cocoa butter and other glycerides) or retention enemas for rectal delivery.

In one embodiment, the GSNOR inhibitors are prepared with carriers that will protect against rapid elimination from the body. For example, a controlled release formulation can be used, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially.

Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

Additionally, suspensions of the GSNOR inhibitors may be prepared as appropriate oily injection suspensions. Suitable lipophilic solvents or vehicles include fatty oils, such as sesame oil, or synthetic fatty acid esters, such as ethyl oleate, triglycerides, or liposomes. Non-lipid polycationic amino polymers may also be used for delivery. Optionally, the suspension may also include suitable stabilizers or agents to increase the solubility of the compounds and allow for the preparation of highly concentrated solutions.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of GSNOR inhibitor calculated to produce the desired therapeutic effect in association with the required pharmaceutical carrier. The specification for the dosage unit forms of the invention are dictated by and directly dependent on the unique characteristics of the GSNOR inhibitor and the particular therapeutic effect to be achieved, and the limitations inherent in the art of compounding such an active agent for the treatment of individuals.

Pharmaceutical compositions according to the invention comprising at least one GSNOR inhibitor can comprise one or more pharmaceutical excipients. Examples of such excipients include, but are not limited to binding agents, filling agents, lubricating agents, suspending agents, sweeteners, flavoring agents, preservatives, buffers, wetting agents, disintegrants, effervescent agents, and other excipients. Such excipients are known in the art. Exemplary excipients include: (1) binding agents which include various celluloses and cross-linked polyvinylpyrrolidone, microcrystalline cellulose, such as Avicel® PH101 and Avicel® PH102, silicified microcrystalline cellulose (ProSolv SMCC™), gum tragacanth and gelatin; (2) filling agents such as various starches, lactose, lactose monohydrate, and lactose anhydrous; (3) disintegrating agents such as alginic acid, Primogel, corn starch, lightly crosslinked polyvinyl pyrrolidone, potato starch, maize starch, and modified starches, croscarmellose sodium, cross-povidone, sodium starch glycolate, and mixtures thereof; (4) lubricants, including agents that act on the flowability of a powder to be compressed, include magnesium stearate, colloidal silicon dioxide, such as Aerosil® 200, talc, stearic acid, calcium stearate, and silica gel; (5) glidants such as colloidal silicon dioxide; (6) preservatives, such as potassium sorbate, methylparaben, propylparaben, benzoic acid and its salts, other esters of parahydroxybenzoic acid such as butylparaben, alcohols such as ethyl or benzyl alcohol, phenolic compounds such as phenol, or quaternary compounds such as benzalkonium chloride; (7) diluents such as pharmaceutically acceptable inert fillers, such as microcrystalline cellulose, lactose, dibasic calcium phosphate, saccharides, and/or mixtures of any of the foregoing; examples of diluents include microcrystalline cellulose, such as Avicel® PH101 and Avicel® PH102; lactose such as lactose monohydrate, lactose anhydrous, and Pharmatose® DCL21; dibasic calcium phosphate such as Emcompress®; mannitol; starch; sorbitol; sucrose; and glucose; (8) sweetening agents, including any natural or artificial sweetener, such as sucrose, saccharin sucrose, xylitol, sodium saccharin, cyclamate, aspartame, and acesulfame; (9) flavoring agents, such as peppermint, methyl salicylate, orange flavoring, Magnasweet® (trademark of MAFCO), bubble gum flavor, fruit flavors, and the like; and (10) effervescent agents, including effervescent couples such as an organic acid and a carbonate or bicarbonate. Suitable organic acids include, for example, citric, tartaric, malic, fumaric, adipic, succinic, and alginic acids and anhydrides and acid salts. Suitable carbonates and bicarbonates include, for example, sodium carbonate, sodium bicarbonate, potassium carbonate, potassium bicarbonate, magnesium carbonate, sodium glycine carbonate, L-lysine carbonate, and arginine carbonate. Alternatively, only the sodium bicarbonate component of the effervescent couple may be present.

E. Kits Comprising the Compositions of the Invention

The present invention also encompasses kits comprising the compositions of the invention. Such kits can comprise, for example, (1) at least one GSNOR inhibitor; and (2) at least one pharmaceutically acceptable carrier, such as a solvent or solution. Additional kit components can optionally include, for example: (1) any of the pharmaceutically acceptable excipients identified herein, such as stabilizers, buffers, etc., (2) at least one container, vial or similar apparatus for holding and/or mixing the kit components; and (3) delivery apparatus, such as an inhaler, nebulizer, syringe, etc.

F. Methods of Preparing GSNOR Inhibitors

The GSNOR inhibitors of the invention can readily be synthesized using known synthetic methodologies or via a modification of known synthetic methodologies. As would be readily recognized by a skilled artisan, the methodologies described below allow the synthesis of chromones having a variety of substituents. Exemplary synthetic methods are described in the examples below.

If needed, further purification and separation of enantiomers and diastereomers can be achieved by routine procedures known in the art. Thus, for example, the separation of enantiomers of a compound can be achieved by the use of chiral HPLC and related chromatographic techniques. Diastereomers can be similarly separated. In some instances, however, diastereomers can simply be separated physically, such as, for example, by controlled precipitation or crystallization.

The process of the invention, when carried out as prescribed herein, can be conveniently performed at temperatures that are routinely accessible in the art. In one embodiment, the process is performed at a temperature in the range of about 25° C. to about 110° C. In another embodiment, the temperature is in the range of about 40° C. to about 100° C. In yet another embodiment, the temperature is in the range of about 50° C. to about 95° C.

Synthetic steps that require a base are carried out using any convenient organic or inorganic base. Typically, the base is not nucleophilic. Thus, in one embodiment, the base is selected from carbonates, phosphates, hydroxides, alkoxides, salts of disilazanes, and tertiary amines.

The process of the invention, when performed as described herein, can be substantially complete after several minutes to after several hours depending upon the nature and quantity of reactants and reaction temperature. The determination of when the reaction is substantially complete can be conveniently evaluated by ordinary techniques known in the art such as, for example, HPLC, LCMS, TLC, and $^1$H NMR.

G. Method of Treatment

The invention encompasses methods of preventing or treating (e.g., alleviating one or more symptoms of) medical conditions through use of one or more of the disclosed compounds. The methods comprise administering a therapeutically effective amount of a GSNOR inhibitor to a patient in need. The compositions of the invention can also be used for prophylactic therapy.

The GSNOR inhibitor used in the methods of treatment according to the invention can be: (1) a novel GSNOR inhibitor described herein, or a pharmaceutically acceptable salt thereof, a prodrug thereof, or a metabolite thereof; (2) a compound which was known prior to the present invention, but wherein it was not known that the compound is a GSNOR inhibitor, or a pharmaceutically acceptable salt thereof, a prodrug thereof, or a metabolite thereof; or (3) a compound which was known prior to the present invention, and wherein it was known that the compound is a GSNOR inhibitor, but wherein it was not known that the compound is useful for the methods of treatment described herein, or a pharmaceutically acceptable salt thereof, a prodrug thereof, or a metabolite thereof.

The patient can be any animal, domestic, livestock or wild, including, but not limited to cats, dogs, horses, pigs and cattle, and preferably human patients. As used herein, the terms patient and subject may be used interchangeably.

In subjects with deleteriously high levels of GSNOR or GSNOR activity, modulation may be achieved, for example, by administering one or more of the disclosed compounds that disrupts or down-regulates GSNOR function, or decreases GSNOR levels. These compounds may be administered with other GSNOR inhibitor agents, such as anti-GSNOR antibodies or antibody fragments, GSNOR antisense, siRNA, or small molecules, or other inhibitors, alone or in combination with other agents as described in detail herein.

The present invention provides a method of treating a subject afflicted with a disorder ameliorated by NO donor therapy. Such a method comprises administering to a subject a therapeutically effective amount of a GSNOR inhibitor.

As used herein, "treating" describes the management and care of a patient for the purpose of combating a disease, condition, or disorder and includes the administration of a compound of the present invention to prevent the onset of the symptoms or complications, alleviating the symptoms or complications, or eliminating the disease, condition or disorder. More specifically, "treating" includes reversing, attenuating, alleviating, minimizing, suppressing or halting at least one deleterious symptom or effect of a disease (disorder) state, disease progression, disease causative agent (e.g., bacteria or viruses), or other abnormal condition. Treatment is continued as long as symptoms and/or pathology ameliorate.

The disorders can include pulmonary disorders associated with hypoxemia and/or smooth muscle constriction in the lungs and/or lung infection and/or lung injury (e.g., pulmonary hypertension, ARDS, asthma, pneumonia, pulmonary fibrosis/interstitial lung diseases, cystic fibrosis, COPD) cardiovascular disease and heart disease, including conditions such as hypertension, ischemic coronary syndromes, atherosclerosis, heart failure, glaucoma, diseases characterized by angiogenesis (e.g., coronary artery disease), disorders where there is risk of thrombosis occurring, disorders where there is risk of restenosis occurring, chronic inflammatory diseases (e.g., AID dementia and psoriasis), diseases where there is risk of apoptosis occurring (e.g., heart failure, atherosclerosis, degenerative neurologic disorders, arthritis and liver injury (ischemic or alcoholic)), impotence, obesity caused by eating in response to craving for food, stroke, reperfusion injury (e.g., traumatic muscle injury in heart or lung or crush injury), and disorders where preconditioning of heart or brain for NO protection against subsequent ischemic events is beneficial.

In one embodiment, the compounds of the present invention or a pharmaceutically acceptable salt thereof, or a prodrug or metabolite thereof, can be administered in combination with an NO donor. An NO donor donates nitric oxide or a related redox species and more generally provides nitric oxide bioactivity, that is activity which is identified with nitric oxide, e.g., vasorelaxation or stimulation or inhibition of a receptor protein, e.g., ras protein, adrenergic receptor, NFκB. NO donors including S-nitroso, O-nitroso, C-nitroso and N-nitroso compounds and nitro derivatives thereof and metal NO complexes, but not excluding other NO bioactivity generating compounds, useful herein are described in "Methods in Nitric Oxide Research," Feelisch et al. eds., pages 71-115 (J. S., John Wiley & Sons, New York, 1996), which is incorporated herein by reference. NO donors which are C-nitroso compounds where nitroso is attached to a tertiary carbon which are useful herein include those described in U.S. Pat. No. 6,359,182 and in WO 02/34705. Examples of S-nitroso compounds, including S-nitrosothiols useful herein, include, for example, S-nitrosoglutathione, S-nitroso-N-acetylpenicillamine, S-nitroso-cysteine and ethyl ester thereof, S-nitroso cysteinyl glycine, S-nitroso-gamma-methyl-L-homocysteine, S-nitroso-L-homocysteine, S-nitroso-gamma-thio-L-leucine, S-nitroso-delta-thio-L-leucine, and S-nitrosoalbumin Examples of other NO donors useful herein are sodium nitroprusside (nipride), ethyl nitrite, isosorbide, nitroglycerin, SIN 1 which is molsidomine, furoxamines, N-hydroxy (N-nitrosamine) and perfluorocarbons that have been saturated with NO or a hydrophobic NO donor.

The combination of a GSNOR inhibitor with R(+) enantiomer of amlodipine, a known NO releaser (Zhang X. P at al. 2002 J. Cardiovascular Pharmacology 39, 208-214) is also an embodiment of the present invention.

The present invention also provides a method of treating a subject afflicted with pathologically proliferating cells where the method comprises administering to said subject a therapeutically effective amount of an inhibitor of GSNOR. The inhibitors of GSNOR are the compounds as defined above, or a pharmaceutically acceptable salt thereof, or a prodrug or metabolite thereof, in combination with a pharmaceutically acceptable carrier. Treatment is continued as long as symptoms and/or pathology ameliorate.

In another embodiment, the pathologically proliferating cells can be pathologically proliferating microbes. The microbes involved can be those where GSNOR is expressed to protect the microbe from nitrosative stress or where a host cell infected with the microbe expresses the enzyme, thereby protecting the microbe from nitrosative stress. The term "pathologically proliferating microbes" is used herein to mean pathologic microorganisms including but not limited to pathologic bacteria, pathologic viruses, pathologic *Chlamydia*, pathologic protozoa, pathologic *Rickettsia*, pathologic fungi, and pathologic mycoplasmata. More detail on the applicable microbes is set forth at columns 11 and 12 of U.S. Pat. No. 6,057,367. The term "host cells infected with pathologic microbes" includes not only mammalian cells infected with pathologic viruses but also mammalian cells containing intracellular bacteria or protozoa, e.g., macrophages containing *Mycobacterium tuberculosis, Mycobacterium* leper (leprosy), or *Salmonella typhi* (typhoid fever).

In another embodiment, the pathologically proliferating cells can be pathologic helminths. The term "pathologic helminths" is used herein to refer to pathologic nematodes, pathologic trematodes and pathologic cestodes. More detail on the applicable helminths is set forth at column 12 of U.S. Pat. No. 6,057,367.

In another embodiment, the pathologically proliferating cells can be pathologically proliferating mammalian cells. The term "pathologically proliferating mammalian cells" as used herein means cells of the mammal that grow in size or number in said mammal so as to cause a deleterious effect in the mammal or its organs. The term includes, for example, the pathologically proliferating or enlarging cells causing restenosis, the pathologically proliferating or enlarging cells causing benign prostatic hypertrophy, the pathologically proliferating cells causing myocardial hypertrophy and proliferating cells at inflammatory sites such as synovial cells in arthritis or cells associated with a cell proliferation disorder.

As used herein, the term "cell proliferative disorder" refers to conditions in which the unregulated and/or abnormal growth of cells can lead to the development of an unwanted condition or disease, which can be cancerous or non-cancerous, for example a psoriatic condition. As used herein, the term "psoriatic condition" refers to disorders involving keratinocyte hyperproliferation, inflammatory cell infiltration, and cytokine alteration. The cell proliferative disorder can be a precancerous condition or cancer. The cancer can be primary cancer or metastatic cancer, or both.

As used herein, the term "cancer" includes solid tumors, such as lung, breast, colon, ovarian, pancreas, prostate, adenocarcinoma, squamous carcinoma, sarcoma, malignant glioma, leiomyosarcoma, hepatoma, head and neck cancer, malignant melanoma, non-melanoma skin cancers, as well as hematologic tumors and/or malignancies, such as leukemia, childhood leukemia and lymphomas, multiple myeloma, Hodgkin's disease, lymphomas of lymphocytic and cutaneous origin, acute and chronic leukemia such as acute lymphoblastic, acute myelocytic or chronic myelocytic leukemia, plasma cell neoplasm, lymphoid neoplasm and cancers associated with AIDS.

In addition to psoriatic conditions, the types of proliferative diseases which may be treated using the compositions of the present invention are epidermic and dermoid cysts, lipomas, adenomas, capillary and cutaneous hemangiomas, lymphangiomas, nevi lesions, teratomas, nephromas, myofibromatosis, osteoplastic tumors, and other dysplastic masses and the like. In one embodiment, proliferative diseases include dysplasias and disorders of the like.

In one embodiment, the treating cancer comprises a reduction in tumor size, decrease in tumor number, a delay of tumor growth, decrease in metastaic lesions in other tissues or organs distant from the primary tumor site, an improvement in the survival of patients, or an improvement in the quality of patient life, or at least two of the above.

In another embodiment, the treating a cell proliferative disorder comprises a reduction in the rate of cellular proliferation, reduction in the proportion of proliferating cells, a decrease in size of an area or zone of cellular proliferation, or a decrease in the number or proportion of cells having an abnormal appearance or morphology, or at least two of the above.

In yet another embodiment, the compounds of the present invention or a pharmaceutically acceptable salt thereof, a prodrug thereof, or metabolite thereof, can be administered in combination with a second chemotherapeutic agent. In a further embodiment, the second chemotherapeutic agent is selected from the group consisting of tamoxifen, raloxifene, anastrozole, exemestane, letrozole, cisplatin, carboplatin, paclitaxel, cyclophosphamide, lovastatin, minosine, gemcitabine, araC, 5-fluorouracil, methotrexate, docetaxel, goserelin, vincristine, vinblastin, nocodazole, teniposide, etoposide, epothilone, navelbine, camptothecin, daunonibicin, dactinomycin, mitoxantrone, amsacrine, doxorubicin, epirubicin, idarubicin imatanib, gefitinib, erlotinib, sorafenib, sunitinib malate, trastuzumab, rituximab, cetuximab, and bevacizumab.

In one embodiment, the compounds of the present invention or a pharmaceutically acceptable salt thereof, a prodrug thereof, or metabolite thereof, can be administered in combination with an agent that imposes nitrosative or oxidative stress. Agents for selectively imposing nitrosative stress to inhibit proliferation of pathologically proliferating cells in combination therapy with GSNOR inhibitors herein and dosages and routes of administration therefor include those disclosed in U.S. Pat. No. 6,057,367, which is incorporated herein. Supplemental agents for imposing oxidative stress (i.e., agents that increase GSSG (oxidized glutathione) over GSH (glutathione) ratio or NAD(P) over NAD(P)H ratio or increase thiobarbituric acid derivatives) in combination therapy with GS-FDH inhibitors herein include, for example, L-buthionine-S-sulfoximine (BSO), glutathione reductase inhibitors (e.g., BCNU), inhibitors or uncouplers of mitochondrial respiration and drugs that increase reactive oxygen species (ROS), e.g., adriamycin, in standard dosages with standard routes of administration.

GSNOR inhibitors may also be co-administered with a phosphodiesterase inhibitor (e.g., rolipram, cilomilast, roflumilast, Viagra® (sildenifil citrate), Cialis® (tadalafil), Levitra® (vardenifil), etc.) a β-agonist, a steroid, or a leukotriene antagonist (LTD-4). Those skilled in the art can readily determine the appropriate therapeutically effective amount depending on the disorder to be ameliorated.

GSNOR inhibitors may be used as a means to improve β-adrenergic signaling. In particular, inhibitors of GSNOR alone or in combination with β-agonists could be used to treat or protect against heart failure, or other vascular disorders such as hypertension and asthma. GSNOR inhibitors can also be used to modulate G protein coupled receptors (GPCRs) by potentiating Gs G-protein, leading to smooth muscle relaxation (e.g., airway and blood vessels), and by attenuating Gq G-protein, and thereby preventing smooth muscle contraction (e.g., in airway and blood vessels).

The therapeutically effective amount for the treatment of a subject afflicted with a disorder ameliorated by NO donor therapy is the GSNOR inhibiting amount in vivo that causes amelioration of the disorder being treated or protects against a risk associated with the disorder. For example, for asthma, a therapeutically effective amount is a bronchodilating effective amount; for cystic fibrosis, a therapeutically effective amount is an airway obstruction ameliorating effective amount; for ARDS, a therapeutically effective amount is a hypoxemia ameliorating effective amount; for heart disease, a therapeutically effective amount is an angina relieving or angiogenesis inducing effective amount; for hypertension, a therapeutically effective amount is a blood pressure reducing effective amount; for ischemic coronary disorders, a therapeutic amount is a blood flow increasing effective amount; for atherosclerosis, a therapeutically effective amount is an endothelial dysfunction reversing effective amount; for glaucoma, a therapeutic amount is an intraocular pressure reducing effective amount; for diseases characterized by angiogenesis, a therapeutically effective amount is an angiogenesis inhibiting effective amount; for disorders where there is risk of thrombosis occurring, a therapeutically effective amount is a thrombosis preventing effective amount; for disorders where there is risk of restenosis occurring, a therapeutically effective amount is a restenosis inhibiting effective amount; for chronic inflammatory diseases, a therapeutically effective amount is an inflammation reducing effective amount; for disorders where there is risk of apoptosis occurring, a therapeutically effective amount is an apoptosis preventing effective amount; for impotence, a therapeutically effective is an erection attaining or sustaining effective amount; for obesity, a therapeutically effective amount is a satiety causing effective amount; for stroke, a therapeutically effective amount is a blood flow increasing or a TIA protecting effective amount; for reperfusion injury, a therapeutically effective amount is a function increasing effective amount; and for preconditioning of heart and brain, a therapeutically effective amount is a cell protective effective amount, e.g., as measured by triponin or CPK.

The therapeutically effective amount for the treatment of a subject afflicted with pathologically proliferating cells means a GSNOR inhibiting amount in vivo which is an antiproliferative effective amount. Such antiproliferative effective amount as used herein means an amount causing reduction in rate of proliferation of at least about 20%, at least about 10%, at least about 5%, or at least about 1%.

In general, the dosage, i.e., the therapeutically effective amount, ranges from 1 μg to 10 g/kg and often ranges from 10 μg to 1 g/kg or 10 μg to 100 mg/kg body weight of the subject being treated, per day.

H. Other Uses

The compounds of the present invention or a pharmaceutically acceptable salt thereof, or a prodrug or metabolite thereof, can be applied to various apparatus in circumstances when the presence of such compounds would be beneficial. Such apparatus can be any device or container, for example, implantable devices in which a GSNOR inhibitor can be used to coat a surgical mesh or cardiovascular stent prior to implantation in a patient. The GSNOR inhibitors of the present invention can also be applied to various apparatus for in vitro assay purposes or for culturing cells.

The compounds of the present invention or a pharmaceutically acceptable salt thereof, or a prodrug or metabolite thereof, can also be used as an agent for the development, isolation or purification of binding partners to GSNOR inhibitor compounds, such as antibodies, natural ligands, and the like. Those skilled in the art can readily determine related uses for the compounds of the present invention.

EXAMPLES

The following Scheme and Examples are given to illustrate the present invention. It should be understood, however, that the invention is not to be limited to the specific conditions or details described in these examples. Throughout the specification, any and all references to a publicly available document, including a U.S. patent, are specifically incorporated by reference.

The GSNOR inhibitors of the invention can readily be synthesized using known synthetic methodologies or via a modification of known synthetic methodologies. As would be readily recognized by a skilled artisan, the methodologies described below allow the synthesis of chromones having a variety of substituents. General scheme I below is a representative procedure for making chromone compounds of the invention. Additional synthetic detail can be found in Examples 1-21, and in the Intermediate section, Example 23.

General Scheme 1

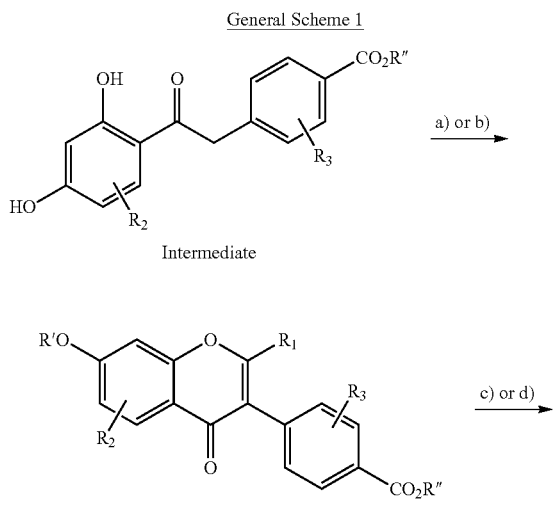

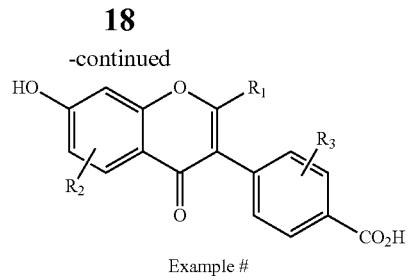

Example #

$R''$ is Et or Me
$R'$ is H or $C(O)R_1$
a) $R_1C(O)OC(O)R_1$, triethylamine, dichloromethane, room temperature, 1-5 h
b) $ClC(O)R_1$, triethylamine, 95° C., 8-20 h
c) Conc. HCl/dioxane, 60-80° C., 7-24 h
d) LiOH, MeOH/THF/water, room temperature, 3-8 h

Example 1

4-(2-(difluoromethyl)-7-hydroxy-4-oxo-4H-chromen-3-yl)benzoic acid

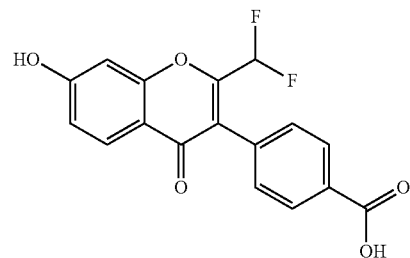 [SMILES: O=C(O)c1ccc(-c2c(C(F)F)oc3cc(O)ccc3c2=O)cc1]

Synthesis: Prepared following General Scheme 1, starting from Intermediate A-1a, using conditions a) (modified) and c).

Step 1: Synthesis of ethyl 4-(2-(difluoromethyl)-7-hydroxy-4-oxo-4H-chromen-3-yl)benzoate: To a solution of Intermediate A-1a (450 mg, 1.5 mmol) and TEA (758 mg, 7.5 mmol) was added 2,2-difluoroacetic anhydride (522 mg, 3.0 mmol). The mixture was stirred at 120° C. for 4 h. The reaction mixture was cooled to room temperature and concentrated in vacuo to afford a brown solid, which was used for next step without further purification (400 mg, 74%).

Step 2: Synthesis of 4-(2-(difluoromethyl)-7-hydroxy-4-oxo-4H-chromen-3-yl)benzoic acid (Example 1), an Example of c) Conditions: To a mixture of ethyl 4-(2-(difluoromethyl)-7-hydroxy-4-oxo-4H-chromen-3-yl)benzoate (400 mg, 1.16 mmol) in 1,4-dioxane (1 mL) was added Conc. HCl (1 mL). The reaction mixture was heated to reflux overnight. The mixture was cooled to room temperature and filtered. The filtered mass was washed with water (5 mL) 2 times and ethanol (2 mL) and purified by prep-HPLC to afford a white solid (50 mg, 13%).

Data: $^1$H NMR (500 MHz, DMSO-$d_6$, TMS): δ 13.11 (s, 1H), 11.09 (s, 1H), 8.02 (d, J=8.5 Hz, 2H), 7.95 (d, J=8.5 Hz, 1H), 7.43 (d, J=8.5 Hz, 2H), 7.01 (dd, J=2.5, 9.0 Hz, 1H), 6.96 (d, J=2.5 Hz, 1H), 6.68 (t, J=51.0 Hz, 1H); MS (ESI): m/z 333.0 [M+1]$^+$.

Example 2

4-(7-hydroxy-2-(methoxymethyl)-4-oxo-4H-chromen-3-yl)benzoic acid

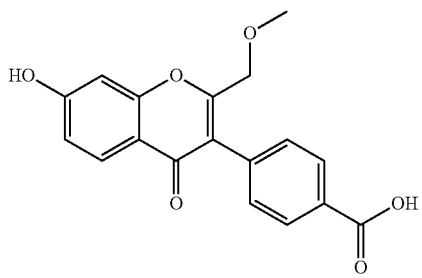 [SMILES: COCc1oc2cc(O)ccc2c(=O)c1-c1ccc(C(=O)O)cc1]

Synthesis: Prepared following General Scheme 1, starting from Intermediate A-1a, using conditions b) (modified) and c).

Step 1: Synthesis of ethyl 4-(7-hydroxy-2-(methoxymethyl)-4-oxo-4H-chromen-3-yl)benzoate, an Example of b) Conditions. To stirred mixture of Intermediate A-1a (450 mg, 1.5 mmol) and $Et_3N$ (825 mg, 7.5 mmol) in DCM (5 mL) was added 2-methoxyacetyl chloride (486 mg, 4.5 mmol). Then the mixture was stirred at room temperature for 5 h. The solution was removed under reduced pressure and the residue was diluted with water (50 mL), extracted with ethyl acetate (50 mL×3). The organic layers were dried over $Na_2SO_4$, concentrated and purified by silica gel column chromatography (PE:EA=1:1) to afford ethyl 4-(7-hydroxy-2-(methoxymethyl)-4-oxo-4H-chromen-3-yl)benzoate as a yellow oil (84 mg, 16%). MS (ESI): m/z 355.0 [M+1]+.

Step 2: Synthesis of 4-(7-hydroxy-2-(methoxymethyl)-4-oxo-4H-chromen-3-yl)benzoic acid (Example 2). General Scheme 1, c) conditions (purified by prep HPLC), see step 2 of Example 1 for detailed example.

Data: $^1$H NMR (MeOH-$d_4$, 500 MHz, TMS): δ 8.08 (d, J=7.5 Hz, 2H), 7.99 (d, J=9.0 Hz, 1H), 7.41 (d, J=7.5 Hz, 2H), 6.94 (t, J=10.0 Hz, 1H), 6.89 (d, J=1.5 Hz, 1H), 4.24 (s, 2H), 3.34 (s, 2H); MS (ESI): m/z 327.1 [M+1]+.

Example 3

4-(7-hydroxy-2-isopropyl-4-oxo-4H-chromen-3-yl)benzoic acid

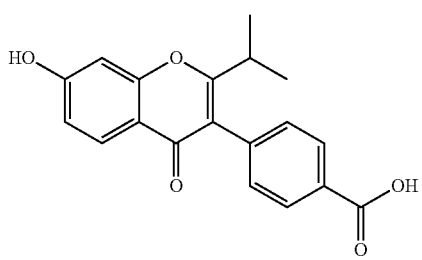 [SMILES: CC(C)c1oc2cc(O)ccc2c(=O)c1-c1ccc(C(=O)O)cc1]

Synthesis: Prepared following General Scheme 1, starting from Intermediate A-1a, using conditions b) and d). Synthetic details included here as an example of b) and d).

Step 1: Synthesis of ethyl 4-(7-(isobutyryloxy)-2-isopropyl-4-oxo-4H-chromen-3-yl)benzoate, an Example of Scheme 1, b) Conditions.

To a solution of Intermediate A-1a (450 mg, crude, 1.5 mmol) and TEA (834 μL, 6 mmol) in dried DCM (5 mL) was added dropwise isobutyryl chloride (480 μL, 4.5 mmol) at room temperature. The mixture was stirred for 3 h. The volatiles were removed under reduced pressure. To the residue was added TEA (5 mL) and heated at 95° C. overnight. Cooled to room temperature and filtered; the filter cake was washed with EA (10 mL). The filtrate was concentrated and purified by Combi-Flash (40 g silica gel, start PE:EA=10:0 to 3:1 gradient, 40 mL/min, 40 min, 1.6 L total solvent volume) to afford ethyl 4-(7-(isobutyryloxy)-2-isopropyl-4-oxo-4H-chromen-3-yl)benzoate as a white solid (80 mg, 13%).

Step 2: Synthesis of 4-(7-hydroxy-2-isopropyl-4-oxo-4H-chromen-3-yl)benzoic acid (Example 3), an Example of Scheme 1, d) Conditions.

To a solution of ethyl 4-(7-(isobutyryloxy)-2-isopropyl-4-oxo-4H-chromen-3-yl)benzoate (80 mg, 0.142 mmol) in THF (2 mL) was added a solution of lithium hydroxide (60 mg, 1.42 mmol) in water (1 mL). The mixture was stirred at room temperature for 3 h. TLC (PE:EA=3:1) indicated that the reaction is complete. The organic solvents were removed under reduced pressure, the basic water layers was extracted with DCM (10 mL×2) and adjusted to pH 4~5 with 1 N HCl solution, the precipitate was collected by filtration, dried in vacuo to give Example 3 as a yellow solid (58 mg, 94%).

Data: $^1$H NMR (DMSO-$d_6$, 500 MHz, TMS): δ 12.99 (s, 1H), 10.80 (s, 1H), 7.99 (d, J=8 Hz, 2H), 7.87 (d, J=8.5 Hz, 1H), 7.38 (d, J=7.5 Hz, 2H), 6.92 (dd, J=8.5 Hz, 2 Hz, 1H), 6.88 (d, J=2 Hz, 1H), 2.75 (m, 1H), 1.21 (s, 3H), 1.19 (s, 3H); MS (ESI): m/z 325.1 [M+1]+.

Example 4

4-(2-cyclopentyl-7-hydroxy-4-oxo-4H-chromen-3-yl)benzoic acid

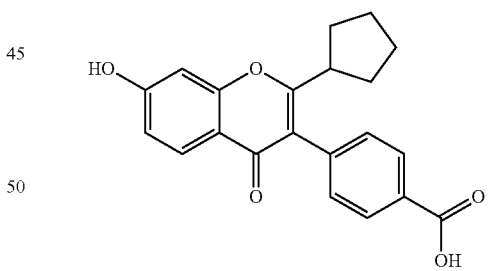

Synthesis: Prepared following General Scheme 1, starting from Intermediate A-1a and cyclopentanecarbonyl chloride in step 1 using condition b) to give ethyl 4-(7-(cyclopentanecarbonyloxy)-2-cyclopentyl-4-oxo-4H-chromen-3-yl)benzoate. Step 2 followed d) conditions. See Example 3 for detailed example.

Data: $^1$H NMR (DMSO-$d_6$, 500 MHz, TMS): δ 12.98 (brs, 1H), 10.79 (brs, 1H), 7.99 (d, J=8.5 Hz, 2H), 7.87 (d, J=9 Hz, 1H), 7.37 (d, J=8 Hz, 2H), 6.91 (dd, J=9 Hz, 2 Hz, 1H), 6.85 (d, J=2 Hz, 1H), 2.84 (m, 1H), 1.78-1.84 (m, 6H), 1.543 (s, 2H); MS (ESI): m/z 351.1 [M+1]+.

Example 5

4-(7-hydroxy-2-methyl-4-oxo-4H-chromen-3-yl)benzoic acid

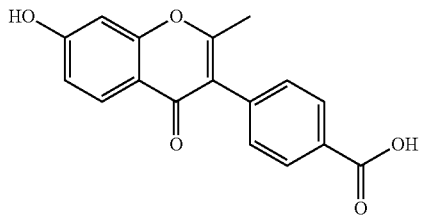 [SMILES: Cc1oc2cc(O)ccc2c(=O)c1-c1ccc(C(=O)O)cc1]

Synthesis: Prepared following General Scheme 1, starting from Intermediate A-1a and acetic anhydride in step 1 using condition a) (where reaction was refluxed for 3 hours after stirring for 2 h at room temperature, and was purified by prep-TLC (PE:EA=3: 1)). Step 2 followed c) conditions. See Example 1 for detailed example.

Data: $^1$H NMR (MeOH-$d_4$, 500 MHz, TMS): δ 8.12 (d, J=8.0 Hz, 2H), 7.99 (d, J=8.5 Hz, 1H), 7.43 (d, J=8.0 Hz, 2H), 6.94 (d, J=9.0 Hz, 1H), 6.88 (s, 1H), 2.32 (s, 3H); MS (ESI): m/z 297.1 [M+1]$^+$.

Example 6

4-(2-benzyl-7-hydroxy-4-oxo-4H-chromen-3-yl)benzoic acid

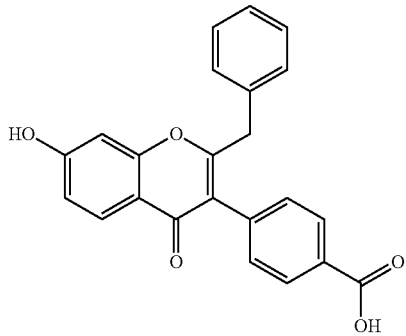 [SMILES: O=C(O)c1ccc(-c2c(Cc3ccccc3)oc3cc(O)ccc3c2=O)cc1]

Synthesis: Prepared following General Scheme 1, starting from Intermediate A-1a and 2-phenylacetyl chloride in Step 1 using condition b) (where reaction was run at room temperature for 3 hours) to give ethyl 4-(2-benzyl-7-hydroxy-4-oxo-4H-chromen-3-yl)benzoate. Step 2: followed d) conditions (where reaction was allowed to stir at room temperature overnight, and was purified by prep-HPLC. See Example 3 for detailed example.

Data: $^1$H NMR (MeOH-$d_4$, 500 MHz): δ 8.12 (d, J=8.0 Hz, 2H), 7.99 (d, J=9.0 Hz, 1H), 7.40 (d, J=8.0 Hz, 2H), 7.29 (q, J=14.5 Hz, 2H), 7.24 (d, J=7.5 Hz, 2H), 7.22 (s, 1H), 7.15 (d, J=6.0 Hz, 2H), 6.94 (q, J=8.5 Hz, 1H), 6.83 (s, 1H), 3.92 (s, 2H); MS (ESI): m/z 373.1 [M+1]$^+$.

Example 7

4-(7-hydroxy-4-oxo-2-(thiophen-2-yl)-4H-chromen-3-yl)benzoic acid

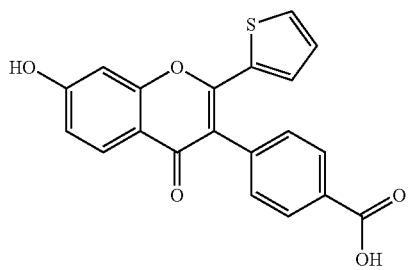 [SMILES: O=C(O)c1ccc(-c2c(-c3cccs3)oc3cc(O)ccc3c2=O)cc1]

Synthesis: Prepared following General Scheme 1, starting from Intermediate A-1a and thiophene-2-carbonyl chloride in step 1 using condition b) to give 3-(4-(ethoxycarbonyl)phenyl)-4-oxo-2-(thiophen-2-yl)-4H-chromen-7-yl thiophene-2-carboxylate. Step 2: followed d) conditions. See Example 3 for detailed example.

Data: $^1$H NMR (DMSO-$d_6$, 500 MHz, TMS): δ 13.08 (brs, 1H), 10.89 (s, 1H), 8.03 (d, J=8 Hz, 2H), 7.90 (d, J=9 Hz, 1H), 7.77 (dd, J=5, 1 Hz, 1H), 7.41 (d, J=8.5 Hz, 2H), 7.31 (dd, J=3.5, 1 Hz, 1H), 7.08 (m, 1H), 6.94~6.98 (m, 2H); MS (ESI): m/z 365.0 [M+1]$^+$.

Example 8

4-(7-hydroxy-4-oxo-2-(thiophen-3-yl)-4H-chromen-3-yl)benzoic acid

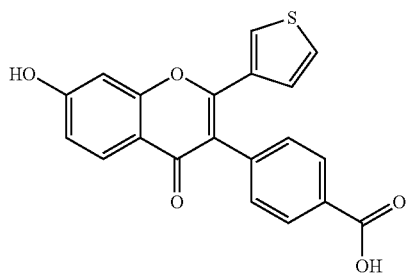 [SMILES: O=C(O)c1ccc(-c2c(-c3ccsc3)oc3cc(O)ccc3c2=O)cc1]

Synthesis: Prepared following General Scheme 1, starting from Intermediate A-1a and thiophene-3-carbonyl chloride in step 1 using condition b) to 3-(4-(ethoxycarbonyl)phenyl)-4-oxo-2-(thiophen-3-yl)-4H-chromen-7-ylthiophene-3-carboxylate. Step 2 followed d) conditions. See Example 3 for detailed example.

Data: $^1$H NMR (DMSO-$d_6$, 500 MHz, TMS): δ 13.01 (brs, 1H), 10.87 (s, 1H), 7.97 (d, J=8 Hz, 2H), 7.92 (d, J=8.5 Hz, 1H), 7.78~7.79 (m, 1H), 7.49~7.51 (m, 1H), 7.35 (d, J=8.5 Hz, 2H), 6.98 (d, J=2 Hz, 1H), 6.95 (dd, J=9, 2 Hz, 1H), 6.70 (dd, J=5.5, 1.5 Hz, 1H); MS (ESI): m/z 365.0 [M+1]$^+$.

Example 9

4-(7-hydroxy-2-isobutyl-4-oxo-4H-chromen-3-yl)benzoic acid

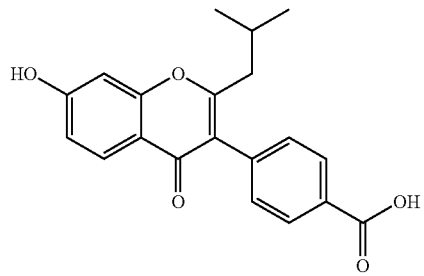 [SMILES: CC(C)Cc1oc2cc(O)ccc2c(=O)c1-c1ccc(C(=O)O)cc1]

Synthesis: Prepared following General Scheme 1, starting from Intermediate A-1a and 3-methylbutanoyl chloride in Step 1 using condition b) to give ethyl 4-(2-isobutyl-7-(3-methylbutanoyloxy)-4-oxo-4H-chromen-3-yl)benzoate. Step 2 followed d) conditions, with purification by recrystallization from PE. See Example 3 for detailed example.

Data: $^1$H NMR (MeOH-d$_4$, 500 MHz, TMS): δ 8.12 (d, J=8.0 Hz, 2H), 8.00 (d, J=9.0 Hz, 1H), 7.39 (d, J=8.0 Hz, 2H), 6.95 (dd, J=2.5, 9.0 Hz, 1H), 6.88 (d, J=2.0 Hz, 1H), 2.49 (d, J=7.0 Hz, 2H), 2.40-2.20 (m, 1H), 0.90 (d, J=7.0 Hz, 6H); MS (ESI): m/z 339.1 [M+1]$^+$.

Example 10

4-(7-hydroxy-4-oxo-2-(trifluoromethyl)-4H-chromen-3-yl)benzoic acid

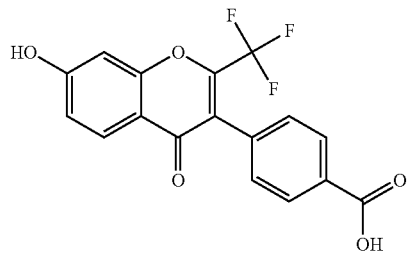 [SMILES: O=C(O)c1ccc(-c2c(C(F)(F)F)oc3cc(O)ccc3c2=O)cc1]

Synthesis: Prepared following General Scheme 1, starting from Intermediate A-1a, using conditions a) and c). Synthetic details included here as another example of a) and c).

Step 1: Synthesis of ethyl 4-(7-hydroxy-4-oxo-2-(trifluoromethyl)-4H-chromen-3-yl)benzoate, Example of a) Conditions. To a solution of Intermediate A-1a (400 mg, 1.33 mmol) in DCM (10 mL) was added TFAA (1.39 g, 6.65 mmol) at 5~10° C. After addition the mixture was stirred at room temperature for 1 h, concentrated and purified by prep-TLC (PE:EA=2:1) to afford product as a yellow solid (280 mg, 56%).

Step 2: Synthesis of 4-(7-hydroxy-4-oxo-2-(trifluoromethyl)-4H-chromen-3-yl)benzoic acid (Example 10), an Example of c) Conditions. To a solution of ethyl 4-(7-hydroxy-4-oxo-2-(trifluoromethyl)-4H-chromen-3-yl)benzoate (23 mg, 0.06 mmol) in dioxane (0.5 mL) was added conc. HCl (0.5 mL). The reaction mixture was stirred at 70° C. for 7 h, cooled to room temperature and centrifuged. The precipitate was rinsed with water (1 mL×2) and dried in vacuo to afford Example 10 as a white solid (13 mg, 61%).

Data: $^1$H NMR (CD$_3$OD, 500 MHz): δ 8.09 (d, J=8.0 Hz, 2H), 8.01 (d, J=9.0 Hz, 1H), 7.38 (d, J=8.0 Hz, 2H), 7.01 (dd, J=9.0, 2.0 Hz, 1H), 6.93 (d, J=2.0 Hz, 1H) ppm. MS (ESI): m/z 351.0 [M+1]$^+$.

Example 11

4-(7-hydroxy-2-(methylthio)-4-oxo-4H-chromen-3-yl)benzoic acid

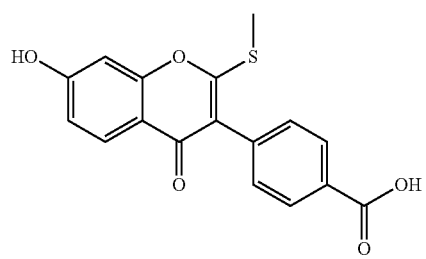 [SMILES: CSc1oc2cc(O)ccc2c(=O)c1-c1ccc(C(=O)O)cc1]

Synthesis: Step 1: Synthesis of methyl 4-(7-methoxy-2-(methylthio)-4-oxo-4H-chromen-3-yl)benzoate. A stirred mixture of Intermediate B (100 mg, 0.33 mmol) and carbon disulfide (127 mg, 1.67 mmol) in DMF (5.0 mL) was cooled to 0° C. and NaH (24 mg, 1.0 mmol) was added. The reaction mixture was stirred at 0° C. for 30 min. Then MeI (94 mg, 0.67 mmol) was added and the reaction mixture was stirred at room temperature for 3 h. The solution was diluted with water (10 mL), extracted with DCM (50 mL×3). The organic layers were dried over Na$_2$SO$_4$, concentrated and purified by silica gel column chromatography (PE:EA=3:1) to afford product (36 mg, not pure), 30%). MS (ESI): m/z 357.0 [M+1]$^+$.

Step 2: Synthesis of 4-(7-hydroxy-2-(methylthio)-4-oxo-4H-chromen-3-yl)benzoic acid (Example 11). Methyl 4-(7-methoxy-2-(methylthio)-4-oxo-4H-chromen-3-yl)benzoate (36 mg, 0.101 mmol) in dry dichloromethane (5.0 mL) was cooled to 0° C. under nitrogen and BBr$_3$ in DCM (1.0 M, 0.2 mL, 0.202 mmol) was added rapidly. Then the mixture was stirred at room temperature overnight. The reaction was quenched with water and concentrated under reduced pressure. The residue was purified by prep-HPLC to afford Example 11 as an off-white solid (8.2 mg, 25%).

Data: $^1$H NMR (MeOH-d$_4$, 500 MHz, TMS): δ 8.10 (d, J=10.0 Hz, 2H), 8.01 (d, J=8.0 Hz, 1H), 7.45 (d, J=8.0 Hz, 2H), 6.97 (d, J=8.0 Hz, 2H), 2.64 (s, 3H); MS (ESI): m/z 329.0 [M+1]$^+$.

Example 12

4-(6-chloro-7-hydroxy-4-oxo-2-(trifluoromethyl)-4H-chromen-3-yl)benzoic acid

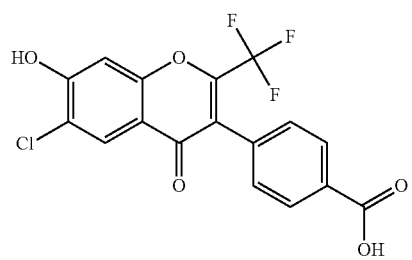 [SMILES: O=C(O)c1ccc(-c2c(C(F)(F)F)oc3cc(O)c(Cl)cc3c2=O)cc1]

Synthesis: Prepared following General Scheme 1, starting from Intermediate C and TFAA in step 1 using condition a) (where reaction was stirred at room temperature for 2 h, then heated at 40° C. for 4 h, and was used without purification). Step 2 followed c) conditions (with purification by prep-HPLC). See Example 10 for detailed example.

Data: ¹H NMR (DMSO-d₆, 500 MHz, TMS): δ 13.10 (brs, 1H), 12.25 (brs, 1H), 8.01 (d, J=8.5 Hz, 2H), 8.00 (s, 1H), 7.42 (d, J=8.0 Hz, 2H), 7.16 (s, 1H); MS (ESI): m/z 384.9 [M+1]⁺.

Example 13

4-(6-fluoro-7-hydroxy-4-oxo-2-(trifluoromethyl)-4H-chromen-3-yl)benzoic acid

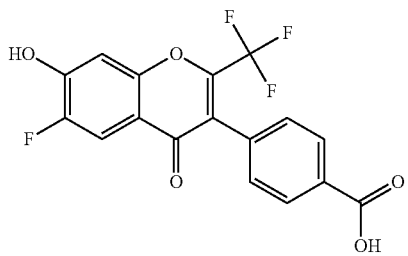 [SMILES: O=C(O)c1ccc(-c2c(C(F)(F)F)oc3cc(O)c(F)cc3c2=O)cc1]

Prepared following General Scheme 1, starting from Intermediate D and TFAA in step 1 using condition a). Step 2 followed c) conditions (with purification by prep-HPLC). See Example 10 for detailed example.

Data: ¹H NMR (MeOH-d₄, 500 MHz, TMS): 8.11 (d, J=7.5 Hz, 2H), 7.77 (d, J=10.5 Hz, 1H), 7.41 (d, J=7.5 Hz, 2H); MS (ESI): m/z 369.0 [M+1]⁺.

Example 14

2-fluoro-4-(7-hydroxy-4-oxo-2-(trifluoromethyl)-4H-chromen-3-yl)benzoic acid

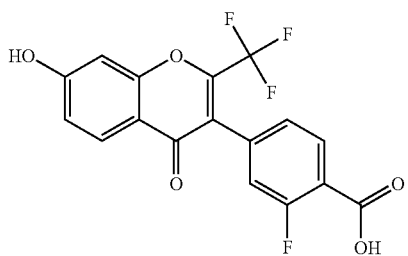 [SMILES: O=C(O)c1ccc(-c2c(C(F)(F)F)oc3cc(O)ccc3c2=O)cc1F]

Synthesis: Prepared following General Scheme 1, starting from Intermediate E and TFAA in step 1 using condition a) (where crude was used without purification). Step 2 followed c) conditions (with aqueous workup, followed by purification by recrystallization from PE:DCM=1:1). See Example 10 for detailed example.

Data: ¹H NMR (MeOH-d₄, 500 MHz, TMS): 8.05~8.01 (m, 2H), 7.22 (d, J=2.0 Hz, 1H), 7.20 (s, 1H), 7.04 (dd, J=2.0 Hz, 9.0 Hz, 1H), 6.96 (d, J=2.0 Hz, 1H); MS (ESI): m/z 369.0 [M+1]⁺.

Example 15

3-chloro-4-(7-hydroxy-4-oxo-2-(trifluoromethyl)-4H-chromen-3-yl)benzoic acid

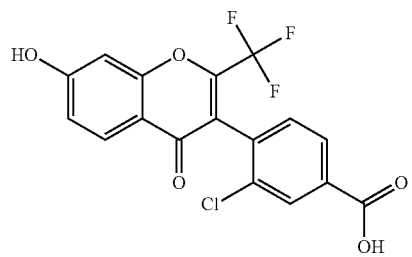 [SMILES: O=C(O)c1ccc(-c2c(C(F)(F)F)oc3cc(O)ccc3c2=O)c(Cl)c1]

Synthesis: Prepared following General Scheme 1, starting from Intermediate F and TFAA in step 1 using condition a) (where an aqueous workup was performed, and crude was used without purification). Step 2 followed c) conditions (with purification by prep-HPLC). See Example 10 for detailed example.

Data: ¹H NMR (DMSO-d₆, 500 MHz, TMS): δ 13.49 (brs, 1H), 11.28 (brs, 1H), 8.04 (d, J=1.0 Hz, 1H), 7.95~7.98 (m, 2H), 7.58 (d, J=8.0 Hz, 1H), 7.06 (dd, J=2.0, 8.5 Hz, 1H), 7.02 (d, J=2.0 Hz, 1H); MS (ESI): m/z 385.0 [M+1]⁺.

Example 16

4-(2-(1,1-difluoroethyl)-7-hydroxy-4-oxo-4H-chromen-3-yl)benzoic acid

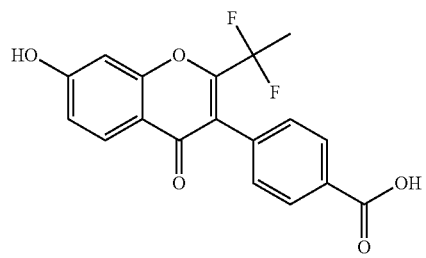 [SMILES: CC(F)(F)c1oc2cc(O)ccc2c(=O)c1-c1ccc(C(=O)O)cc1]

Synthesis: Step 1: To a solution of 2,2-difluoropropanoic acid (330 mg, 2.97 mmol) in DCM (5 mL) was added P₂O₅ (3.3 g, 29.7 mmol) at room temperature and the mixture was stirred for 2 days to give 2,2-difluoropropanoic anhydride. To a suspension of Intermediate A-2a (170 mg, 0.59 mmol) in TEA (5 mL) was added dropwise the 2,2-difluoropropanoic anhydride in DCM at 0~10° C. The mixture was stirred at room temperature for 2 h. The volatiles were evaporated and the residue was purified by prep-TLC (PE:EA=1:1) to afford methyl 4-(2-(1,1-difluoroethyl)-7-hydroxy-4-oxo-4H-chromen-3-yl)benzoate as brown oil (45 mg, 21%).

Step 2: followed c) conditions (with purification by recrystallization from DCM). See Example 10 for detailed example.

Data: ¹H NMR (MeOH-d₄, 500 MHz, TMS): δ 8.07 (d, J=8.5 Hz, 2H), 8.01 (d, J=8.5 Hz, 1H), 7.37 (d, J=8.5 Hz, 1H), 7.01 (dd, J=2.0, 8.5 Hz, 1H), 6.96 (d, J=2.0 Hz, 1H), 1.95 (t, $J_{F-H}$=18.5 Hz, 3H); MS (ESI): m/z 347.0 [M+1]⁺.

Example 17

4-(7-hydroxy-6-methoxy-4-oxo-2-(trifluoromethyl)-4H-chromen-3-yl)benzoic acid

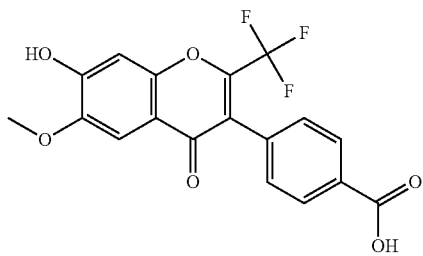 [SMILES: COc1cc2c(=O)c(-c3ccc(C(=O)O)cc3)c(C(F)(F)F)oc2cc1O]

Synthesis: Prepared following General Scheme 1, starting from Intermediate G and TFAA in step 1 using condition a). Step 2 followed c) conditions (with purification by prep-HPLC). See Example 10 for detailed example.

Data: $^1$H NMR (MeOH-d$_4$, 500 MHz, TMS): δ 8.12 (d, J=8.0 Hz, 2H), 7.52 (s, 1H), 7.42 (d, J=8.5 Hz, 2H), 7.04 (s, 1H), 3.98 (s, 3H); MS (ESI): m/z 381.0 [M+1]$^+$.

Example 18

2-chloro-4-(7-hydroxy-4-oxo-2-(trifluoromethyl)-4H-chromen-3-yl)benzoic acid

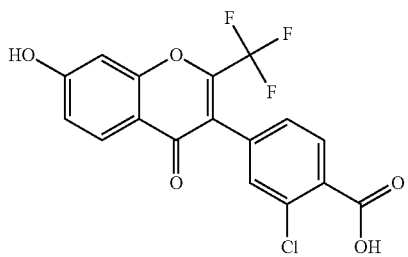 [SMILES: O=C(O)c1ccc(-c2c(C(F)(F)F)oc3cc(O)ccc3c2=O)cc1Cl]

Synthesis: Prepared following General Scheme 1, starting from Intermediate H and TFAA in step 1 using condition a). Step 2 followed c) conditions (with purification by recrystallization from DCM). See Example 10 for detailed example.

Data: $^1$H NMR (MeOH-d$_4$, 500 MHz, TMS): 8.15 (d, J=1.5 Hz, 1H), 8.06~8.04 (m, 2H), 7.47 (d, J=8.5 Hz, 1H), 7.06 (dd, J=2.5, 9.0 Hz, 1H), 6.99 (d, J=2.0 Hz, 1H); MS (ESI): m/z 385.0 [M+1]$^+$.

Example 19

4-(2-(1,1-difluoropropyl)-7-hydroxy-4-oxo-4H-chromen-3-yl)benzoic acid

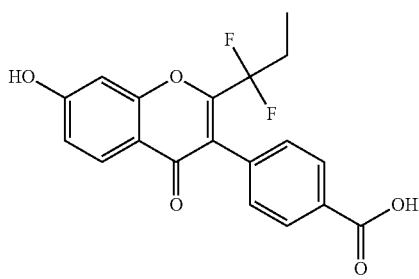 [SMILES: CCC(F)(F)c1oc2cc(O)ccc2c(=O)c1-c1ccc(C(=O)O)cc1]

Synthesis: Step 1: A stirred solution of 2,2-difluorobutanoic acid (500 mg, 4.032 mmol) in CH$_2$Cl$_2$ (30 mL) was treated with P$_2$O$_5$ (5.73 g, 40.32 mmol) at room temperature. The reaction mixture was stored at 5° C. for 2 days. The clear layer was added into a solution of Intermediate A-2 (300 mg, 1.049 mmol) in TEA (0.4 mL, 2.77 mmol); the solid was washed with CH$_2$Cl$_2$ (1 mL×3) and the combined DCM solutions were also added into the solution of Intermediate A-2. The reaction was stirred at room temperature for 2 h. The volatiles were removed under reduced pressure. The residue was taken up in dilute HCl solution and extracted with EA. The extracts were concentrated to afford 300 mg of orange solid, which was purified by silica gel column (PE:EA=10:1 to 4:1) to afford 40 mg of product (yield: 10%).

Step 2: followed c) conditions (with purification by recrystallization from DCM). See Example 10 for detailed example.

Data: $^1$H NMR (MeOH-d$_4$, 500 MHz, TMS): δ 7.96 (d, J=8.5 Hz, 2H), 7.90 (d, J=9.0 Hz, 2H), 7.24 (d, J=8.0 Hz, 2H), 6.89 (dd, J=2.0, 9.0 Hz, 1H), 6.82 (d, J=2.0 Hz, 1H), 2.17-2.09 (m, 2H), 0.91 (t, J=7.5 Hz, 3H); MS (ESI): m/z 347.0 [M+1]$^+$.

Example 20

4-(7-hydroxy-4-oxo-2-(trifluoromethyl)-4H-chromen-3-yl)-3-methoxybenzoic acid

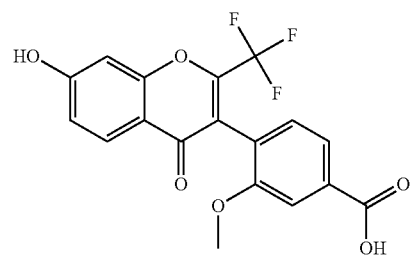 [SMILES: COc1cc(C(=O)O)ccc1-c1c(C(F)(F)F)oc2cc(O)ccc2c1=O]

Synthesis: Prepared following General Scheme 1, starting from Intermediate I and TFAA in step 1 using condition a). Step 2 followed c) conditions. See Example 10 for detailed example.

Data: $^1$H NMR (DMSO-d$_6$, 500 MHz, TMS): δ 13.17 (brs, 1H), 11.21 (brs, 1H), 7.93 (d, J=9.0 Hz, 1H), 7.61 (dd, J=1.0, 7.5 Hz, 1H), 7.58 (s, 1H), 7.32 (d, J=8.0 Hz, 1H), 7.04 (dd, J=2.0, 8.5 Hz, 1H), 6.98 (d, J=1.5 Hz, 1H), 3.77 (s, 3H); MS (ESI): m/z 381.1 [M+1]$^+$.

Example 21

4-(6-cyano-7-hydroxy-4-oxo-2-(trifluoromethyl)-4H-chromen-3-yl)benzoic acid

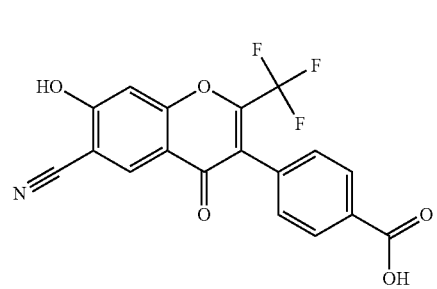 [SMILES: N#Cc1cc2c(=O)c(-c3ccc(C(=O)O)cc3)c(C(F)(F)F)oc2cc1O]

Synthesis: Step 1: Synthesis of methyl 4-(6-bromo-7-methoxy-4-oxo-2-(trifluoromethyl)-4H-chromen-3-yl)benzoate. Prepared following General Scheme 1, starting from Intermediate J and TFAA using condition a) (where crude was purified by silica gel column (PE/EA=10/1 to 3/1).

Step 2: Synthesis of methyl 4-(6-cyano-7-methoxy-4-oxo-2-(trifluoromethyl)-4H-chromen-3-yl)benzoate. To a solution of methyl 4-(6-bromo-7-methoxy-4-oxo-2-(trifluoromethyl)-4H-chromen-3-yl)benzoate (350 mg, 0.76 mmol) in NMP (3 mL) was added CuCN (340 mg, 3.8 mmol). The mixture was stirred at 150° C. for 8 h under the protection of nitrogen. The mixture was cooled to room temperature and quenched with water (10 mL) and filtered. The cake was washed with acetone (15 mL×2). The filtrate was concentrated in vacuo to give brown oil, which was purified by prep-TLC (PE/EA=5/1) to give product (125 mg, 40%) as a yellow solid. MS (ESI): 404.0 [M+1]$^+$.

Step 3: Synthesis of 4-(6-cyano-7-hydroxy-4-oxo-2-(trifluoromethyl)-4H-chromen-3-yl)benzoic acid. To a solution of methyl 4-(6-cyano-7-methoxy-4-oxo-2-(trifluoromethyl)-4H-chromen-3-yl)benzoate (120 mg, 0.29 mmol) in DCM (3 mL) was added dropwise BBr$_3$ (0.35 mL, 4.5 mmol) carefully at room temperature. When the addition was complete, the mixture was stirred for two days. Water was added carefully and the resultant mixture was extracted with ethyl acetate (10 mL×2). The combined organic phase was washed with brine (5 mL), dried over Na$_2$SO$_4$ and concentrated to give brown oil, which was purified by prep-HPLC to afford Example 21 (30 mg, 27.8%) as a yellow powder.

Data: $^1$H NMR (MeOH-d$_4$, 500 MHz, TMS): δ 8.38 (s, 1H), 8.11 (d, J=8.0 Hz, 2H), 7.41 (s, J=8.0 Hz, 2H), 7.09 (s, 1H); MS (ESI): m/z 376.0 [M+1]$^+$.

Example 22

4-(7-hydroxy-4-oxo-4H-chromen-3-yl)benzoic acid

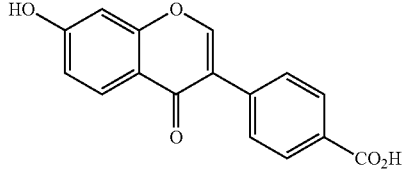 [SMILES: O=C(O)c1ccc(-c2coc3cc(O)ccc3c2=O)cc1]

Synthesis: Step 1: Synthesis of ethyl 4-(7-hydroxy-4-oxo-4H-chromen-3-yl)benzoate. To a solution of Intermediate A-1a (300 mg, 1.0 mmol) in dried DMF (8 mL) was added BF$_3$.Et$_2$O (1.2 mL) carefully at 10° C. with stirring, after the addition was complete, the mixture was warmed to rt for 0.5 h. Then the reaction solution was heated to 60° C. and MsCl (2 mL in 4 mL of DMF) was added. Then the reaction solution was heated to 95° C. for 5 h. The reaction mixture was cooled to room temperature and poured into ice-water (30 mL) and extracted with EA (20 mL×5). The organic phase was washed with brine (20 mL), dried and concentrated in vacuo to give brown oil (160 mg, 51.6%). MS (ESI): m/z 311.0 [M+1]$^+$.

Step 1: Synthesis of 4-(7-hydroxy-4-oxo-4H-chromen-3-yl)benzoic acid (Compound 22). To a mixture of compound ethyl 4-(7-hydroxy-4-oxo-4H-chromen-3-yl)benzoate (160 mg, 0.52 mmol) in 1,4-dioxane (4 mL) was added Conc. HCl (2 mL). The reaction mixture was headed to reflux overnight. The mixture was cooled to room temperature and filtered. The filtered mass was washed with water (5 mL) 2 times and ethanol (2 mL) and dried in vacuo to afford Example 22 as a brown solid (47.3 mg, 32.5%). $^1$H NMR (MeOH-d$_4$, 400 MHz, TMS): δ 8.32 (s, 1H), 8.10 (d, J=8 Hz, 3H), 7.71 (d, J=8.4 Hz, 2H), 6.99 (d, J=11.2 Hz, 1H), 6.91 (s, 1H); MS (ESI): m/z 283.1 [M+1]$^+$.

This Example is included as a comparative example. The IC$_{50}$ for this compound as determined by the method described in Example 24 was 135 nM.

Example 23

Synthesis of Intermediates

The syntheses of the intermediates referenced in the above examples are described here. Exemplary detailed methods are described in Methods 1-3 shown below in the description of Intermediate A-1a and Intermediate A-2a.

General Structure of Intermediates

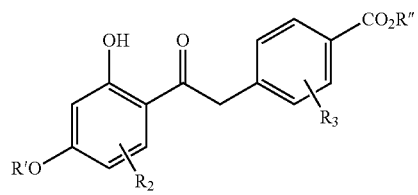

Synthesis of Intermediate A-1a: ethyl 4-(2-(2,4-dihydroxyphenyl)-2-oxoethyl)benzoate) and Intermediate A-2a: methyl 4-(2-(2,4-dihydroxyphenyl)-2-oxoethyl)benzoate)

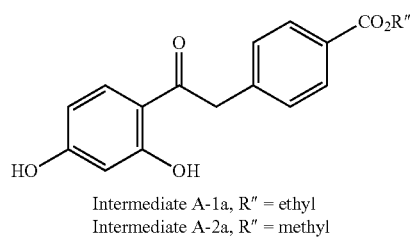

Intermediate A-1a, R″ = ethyl
Intermediate A-2a, R″ = methyl

The Intermediate A-1a was first synthesized by Method 1, then later prepared by the shorter procedure described in Method 2. Method 3 describes the methyl ester Intermediate A-2a in another procedure.

Method 1: Synthesis of ethyl 4-(2-(2,4-dihydroxyphenyl)-2-oxoethyl)benzoate

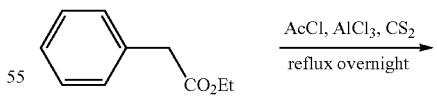

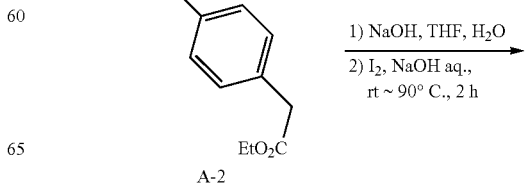

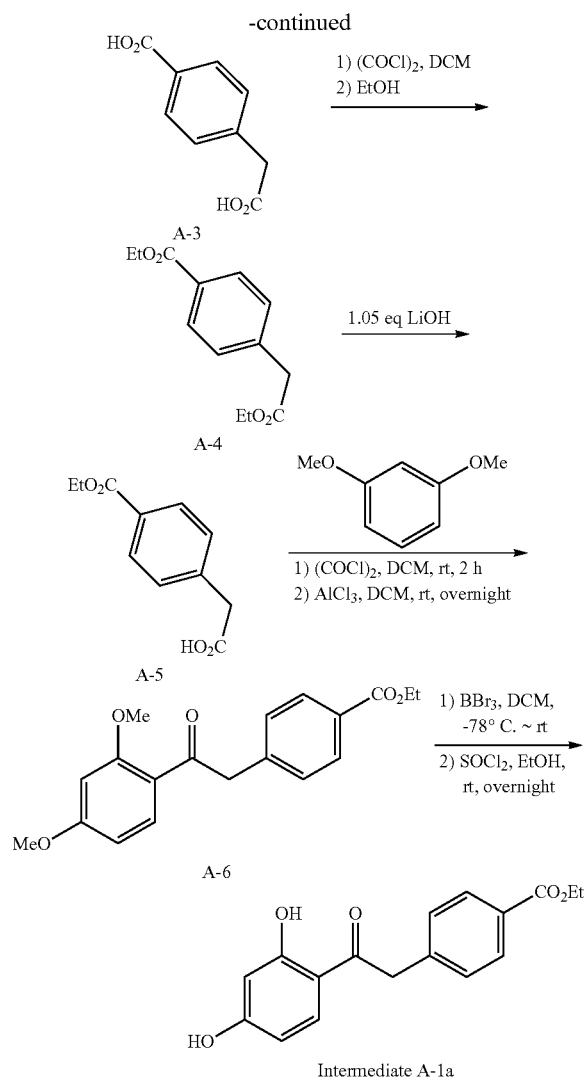

Intermediate A-1a

Step 1: Synthesis of ethyl 2-(4-acetylphenyl)acetate (A-2). To a solution of ethyl 2-phenylacetate (A-1) (50.9 g, 305 mmol) in $CS_2$ (220 mL) was added $AlCl_3$ (93.6 g, 702 mmol) at 0~10° C. over 10 min. After addition, acetyl chloride (30.5 mL, 427 mmol) was added at 0~10° C. over 10 min. After addition, the reaction mixture was slowly heated to reflux overnight, then poured into ice-cooled 5N HCl solution (600 mL), extracted with EA (200 mL×3). The combined organic phase was washed with water (200 mL), sat. $NaHCO_3$ (200 mL) and brine (200 mL), dried over $Na_2SO_4$, concentrated to afford a brown oil. Recrystallized with PE/acetone (150 mL/20 mL) in refrigerator to afford A-2 as a yellow crystal solid (13.8 g, 19%).

Step 2: Synthesis of 4-(carboxymethyl)benzoic acid (A-3). To a solution of A-2 (10.0 g, 48.5 mmol) in $THF/H_2O$ (v/v=1/1, 100 mL) was added NaOH (3.88 g, 97.0 mmol). The reaction solution was stirred at room temperature overnight. THF was removed under reduced pressure, then NaOH (17.46 g, 436.5 mmol) and water (150 mL) was added. Iodine was added portion wise at room temperature. After addition, the reaction mixture was stirred at room temperature for 30 min, then at 90° C. for 2 h. Cooled to room temperature and filtered. The filtrate was adjusted to pH=8~9 with conc. HCl. $NaHSO_3$ solid was added portion wise till the color of reaction mixture changed from brown to yellow. Conc. HCl was added to pH=2~3. The resultant precipitate was filtered, washed with water (10 mL×2), dried in vacuo to afford A-3 as a yellow powder (4.47 g, 50%).

Step 3: Synthesis of ethyl 4-(2-ethoxy-2-oxoethyl)benzoate (A-4). To a solution of A-3 (5.0 g, 27.7 mol) in DCM (50 mL) was added oxalyl chloride (12.6 g, 99.2 mmol) and one drop of DMF. The mixture was stirred at room temperature for 2 h, and then concentrated to dryness. EtOH (100 mL) was added and the mixture was stirred at room temperature for 2 h, then concentrated to dryness and purified to by silica gel column chromatography (PE:EA=5:1) to afford A-4 as a brown oil (4.587 g, 70%).

Step 4: Synthesis of 2-(4-(ethoxycarbonyl)phenyl)acetic acid (A-5). To a solution of A-4 (3.924 g, 16.6 mmol) in $THF/H_2O/EtOH$ (v/v=6/6/1, 65 mL) was added $LiOH \cdot H_2O$ (731 mg, 17.4 mmol). The reaction solution was stirred at room temperature overnight. The THF was removed under reduced pressure and the aqueous solution was acidified with 1N HCl to pH=3. The solid was filtered and dried in vacuo to afford A-5 as a yellow solid (3.02 g, 87%).

Step 5: Synthesis of ethyl 4-(2-(2,4-dimethoxyphenyl)-2-oxoethyl)benzoate (A-6). To a solution of A-5 (3.02 g, 14.5 mmol) in DCM (45 mL) was added oxalyl chloride (7.36 g, 58.0 mmol) and one drop of DMF. The mixture was stirred at room temperature for 2 h, and then concentrated to dryness. The residue was dissolved in DCM (100 mL), $AlCl_3$ (3.48 g, 26.1 mmol) and 1,3-dimethoxybenzene (4.0 g, 29.0 mmol) were added at 0° C. After addition, the mixture was stirred at room temperature overnight. 1N HCl solution (100 mL) was added, extracted with DCM (50 mL×3). The combined organic phase was washed with sat. $NaHCO_3$ (80 mL) and brine (50 mL), dried over $Na_2SO_4$, concentrated and purified by silica gel column chromatography (PE:EA=10:1) to afford A-6 as a brown oil (3.301 g, 69%).

Step 6: Synthesis of ethyl 4-(2-(2,4-dihydroxyphenyl)-2-oxoethyl)benzoate (A-7). To a solution of A-6 (3.30 g, 10.0 mmol) in DCM (50 mL) was added $BBr_3$ (25.05 g, 100.0 mmol) at −78° C. After addition, the mixture was warmed up to room temperature and stirred overnight. 1N HCl solution (100 mL) was added carefully. The mixture was concentrated to dryness. The residue was dissolved in EtOH (200 mL) concentrated to dryness again. This operation repeat twice and the residue was dissolved in EtOH (80 mL). $SOCl_2$ (35.69 g, 300.0 mmol) was added at 10° C. The mixture was stirred at room temperature overnight, concentrated and purified by silica gel column chromatography (PE:EA=5:1) to afford A-7 (Intermediate A-1a) as a yellow solid (2.48 g, 82%).

Method 2Synthesis of ethyl 4-(2-(2,4-dihydroxyphenyl)-2-oxoethyl)benzoate

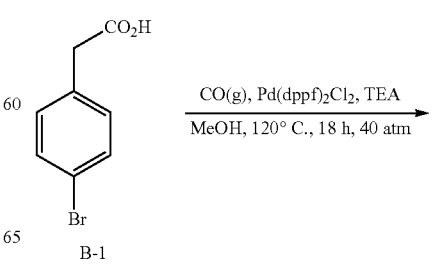

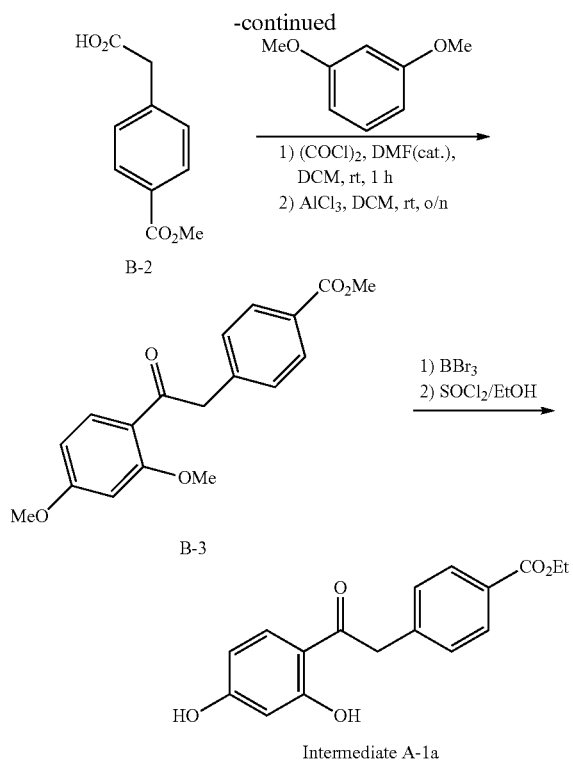

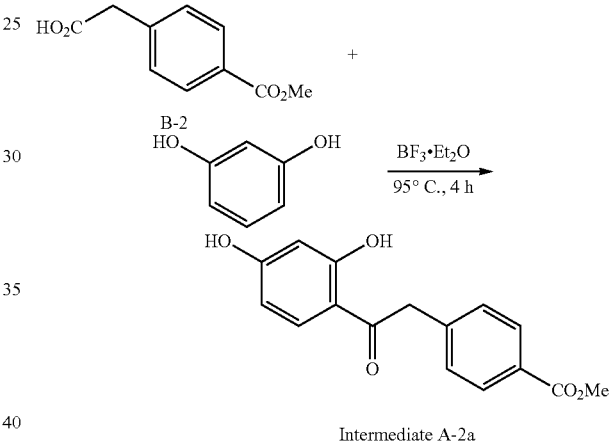

Intermediate A-2a

Step 1: Synthesis of 2-(4-(methoxycarbonyl)phenyl)acetic acid (B-2).

To a solution of 2-(4-bromophenyl)acetic acid (B-1) (91.3 g, 0.42 mol, 1.0 eq) in MeOH (1.5 L) was added dry TEA (85.8 g, 0.85 mol, 2.0 eq) and Pd(dppf)Cl$_2$ (3.43 g, 4.2 mmol, 1%). The solution was heated under CO gas (4 MPa) at 120° C. for 16 h. Then it was filtered and concentrated in vacuo. The residue was dissolved in 500 mL of EA and 1 L of water. The mixture was neutralized by sat. NaHCO$_3$ to pH=7.5 and separated. The inorganic phase was extracted with EA (500 mL×3) acidified with 1N HCl to pH=5. Filtration and drying in vacuo afforded 62.8 g of B-2 (white solid, yield 76%). MS (ESI): m/z 195.1 [M+1]$^+$.

Step 2: Synthesis of methyl 4-(2-(2,4-dimethoxyphenyl)-2-oxoethyl)benzoate (B-3). To a solution of B-2 (15 g, 77.3 mmol) and DMF (1 drop) in anhydrous DCM (150 mL) was added dropwise oxalyl chloride (33 mL, 386.0 mmol) at 0~5° C. with stirring. After the addition was complete, the mixture was stirred at room temperature for 2 h. TLC (PE/EA=3/1, quenched with MeOH) indicated that the reaction was complete, the volatiles were evaporated and the residue was diluted with DCM (20 mL), which was used directly for next step.

To a suspension of aluminum trichloride (16.5 g, 123.7 mmol) in anhydrous DCM (80 mL) was added 1,3-dimethoxybenzene (21.3 g, 154.6 mmol) at 5° C., followed by above acyl chloride solution. The mixture was stirred at room temperature overnight, poured carefully into icy 1 N HCl (200 mL) and extracted with EA (150 mL×3). The combined organic layers were washed with brine (200 mL), dried with anhydrous sodium sulfate, filtered and concentrated to obtain brown oil, which was purified by silica gel column (PE/EA=5/1) to afford B-3 (12 g, 49.6%) as a yellow solid. MS (ESI): m/z 315.1 [M+1]$^+$.

Step 3: Synthesis of ethyl 4-(2-(2,4-dihydroxyphenyl)-2-oxoethyl)benzoate (Intermediate A-1a). To a solution of B-3 (55 g, 141.6 mmol) in DCM (600 mL) was added dropwise BBr$_3$ (164 mL, 1.7 mol) at −10° C. When the addition was complete, the mixture was stirred at room temperature overnight and poured into crashed ice (700 g) with stirring. The volatiles were evaporated to afford a yellow solid, which was dried in high vacuo and dissolved in absolute ethanol (500 mL). To the solution was added dropwise thionyl chloride (80 mL) at 0~10° C. When the addition was complete, the resultant mixture was heated to reflux for 3 h. The volatiles were evaporated and the residue was partitioned between EA (600 mL) and saturated sodium carbonate (200 mL). The organic phase was separated, washed with brine (200 mL), dried with anhydrous sodium sulfate, filtered and concentrated to afford brown slurry, which was purified by SGC (PE/EA=3/1) to afford Intermediate A-1a (24.5 g, 58%) as a yellow solid. $^1$H NMR (CDCl$_3$, 500 MHz, TMS): δ 12.58 (s, 1H), 8.01 (d, J=8.5 Hz, 2H), 7.69 (d, J=9.0 Hz, 1H), 7.33 (d, J=8.0 Hz, 2H), 7.05 (brs, 1H), 6.41 (d, J=8.0 Hz, 1H), 6.37 (s, 1H), 4.38 (q, J=7.0 Hz, 2H), 4.26 (s, 2H), 1.38 (t, J=7 Hz, 3H). MS (ESI): m/z 301.1 [M+1]$^+$.

Method 3 Synthesis of methyl 4-(2-(2,4-dihydroxyphenyl)-2-oxoethyl)benzoate:

Synthesis of methyl 4-(2-(2,4-dihydroxyphenyl)-2-oxoethyl)benzoate (Intermediate A-2a): To a solution of B-2 (see Method 2, step 1 for synthesis) (50 g, 257.5 mmol) in BF$_3$-Et$_2$O (150 mL) was added resorcinol (28.4 g, 257.5 mmol) at room temperature and the mixture was heated at 95° C. for 5.5 h. The mixture was cooled to room temperature and poured into icy 10% Na$_2$CO$_3$ solution (600 mL) with stirring and extracted with EA (500 mL×4). The combined organic layers was washed with water (500 mL×3) and brine (500 mL×2), dried over Na$_2$SO$_4$, filtered and concentrated. The residue was purified by silica gel column (PE:EA=7:1 to 4:1) to afford Intermediate A-2a as a yellow solid (10.2 g, 13.8%). $^1$H NMR (DMSO-d$_6$, 500 MHz): δ 12.38 (s, OH), 10.72 (s, OH), 7.91~7.95 (m, 3H), 7.43 (d, J=8 Hz, 1H), 6.41 (d, J=8.5 Hz, 1H), 6.28 (d, J=1 Hz, 1H), 4.42 (s, 2H), 3.84 (s, 3H); MS (ESI): m/z 287.1 [M+1]$^+$.

Synthesis of Intermediate B: methyl 4-(2-(2-hydroxy-4-methoxyphenyl)-2-oxoethyl)benzoate. To a solution of methyl 4-(2-(2,4-dimethoxyphenyl)-2-oxoethyl)benzoate (B-3, see Method 2 of Intermediate A-1a) (2.5 g, 8.0 mmol) in DCM (25 mL) was added BBr$_3$/DCM (8 mL, 8 mmol, 1 mol/L in DCM) at −78° C. When the addition was complete, the mixture was allowed to warm to room temperature and stirred for 1 h. 1N HCl solution (10 mL) was added carefully. The mixture was washed with sat. Na$_2$CO$_3$ (20 mL), and brine (20 mL), dried over Na$_2$SO$_4$, filtered, concentrated to dryness. The crude was purified by combiflash (PE:EA=10:1) to afford Intermediate B as a yellow solid (600 mg, 25%). $^1$H NMR (CDCl$_3$, 500 MHz, TMS): δ 12.60 (s, 1H) 8.01 (d, J=8.0 Hz, 2H), 7.71 (d, J=9.0 Hz, 1H), 7.34 (d, J=8.0 Hz, 2H), 6.42 (d, J=9.0 Hz, 2H), 4.27 (s, 2H), 3.90 (s, 3H), 3.83 (s, 3H); MS (ESI): m/z 301.1 [M+1]$^+$.

Synthesis of Intermediate C: methyl 4-(2-(5-chloro-2,4-dihydroxyphenyl)-2-oxoethyl)benzoate. Followed the procedure described in Method 3, Intermediate A-2a, starting with B-2 and 4-chlorobenzene-1,3-diol. Crude product was used without purification. MS (ESI): m/z 321.0 [M+1]$^+$.

Synthesis of Intermediate D: methyl 4-(2-(5-fluoro-2,4-dihydroxyphenyl)-2-oxoethyl)benzoate. Followed the procedure described in Method 3, Intermediate A-2, starting with B-2 and 4-fluorobenzene-1,3-diol. MS (ESI): m/z 305.0 [M+1]$^+$.

Synthesis of Intermediate E: methyl 4-(2-(2,4-dihydroxyphenyl)-2-oxoethyl)-2-fluorobenzoate Step 1: Synthesis of 1-bromo-4-(bromomethyl)-2-fluorobenzene. To a solution of 1-bromo-2-fluoro-4-methylbenzene (2.5 g, 13.3 mmol) in trifluoromethyl benzene (25 mL) was a mixture of NBS (2.35 g, 13.3 mmol) and AIBN (945 mg, 6.7 mmol) in five portions at 85° C. for 30 min. The mixture was stirred at 85° C. for 3 h. The insoluble was filtered off and the filtrate was evaporated to afford 1-bromo-4-(bromomethyl)-2-fluorobenzene (2.7 g, 77%) as light yellow oil, which was used directly for next step.

Step 2: Synthesis of methyl 2-fluoro-4-(2-methoxy-2-oxoethyl)benzoate. To a solution of 1-bromo-4-(bromomethyl)-2-fluorobenzene (5.4 g, 20.4 mmol) in MeOH (150 mL) was added TEA (2.8 mL, 20.4 mmol) and Pd(dppf)Cl$_2$ (1.3 g, 2 mmol). The mixture was stirred at 60° C. under CO (0.5 MPa) for 2 h. Additional TEA (4.3 mL, 30.6 mmol) was added and the mixture was heated to 120° C. under CO (4 MPa) for 20 h. Solvent removed in vacuo and the residue was purified by Combi-Flash (80 g silica gel, start PE/EA =10:0 to 1:3 gradient, 60 mL/min, 60 min, 3.6 L total solvent volume) to afford product as a colorless oil (1.5 g, 33%). MS (ESI): m/z 227.1 [M+1]$^+$.

Step 3: Synthesis of 2-(3-fluoro-4-(methoxycarbonyl)phenyl)acetic acid. Followed procedure described in conversion of compound A-4 to compound A-5 in Method 1 of Synthesis of Intermediate A-1a. MS (ESI): m/z 213.0 [M+1]$^+$.

Step 4: Synthesis of methyl 4-(2-(2,4-dihydroxyphenyl)-2-oxoethyl)-2-fluorobenzoate (Intermediate E). Followed procedure described in Method 3 (see Intermediate A-2a), using 2-(3-fluoro-4-(methoxycarbonyl)phenyl)acetic acid where reaction was stirred at 60° C. overnight and at 95° C. for 2 h). $^1$H NMR (CDCl3-d$_6$, 500 MHz, TMS): δ 12.47 (d, J=2.0 Hz, 1H), 7.94 (t, J=8.0 Hz, 1H), 7.69 (d, J=8.5 Hz, 1H), 7.13 (d, J=8.0 Hz, 1H), 7.08 (d, J=11.5 Hz, 1H), 6.43 (d, J=2.5 Hz, 1H), 6.41 (d, J=2.0 Hz, 1H), 4.26 (s, 2H), 3.94 (d, J=2.5 Hz, 3H); MS (ESI): m/z 305.1 [M+1]$^+$.

Synthesis of Intermediate F: methyl 3-chloro-4-(2-(2,4-dihydroxyphenyl)-2-oxoethyl)benzoate.

Step 1: Synthesis of methyl 3-chloro-4-methylbenzoate. To a solution of 3-chloro-4-methylbenzoic acid (20 g, 117 mmol) in MeOH (200 mL) was added dropwise thionyl chloride (25.6 mL, 352 mmol) at 0° C. with stirring. The mixture was stirred at room temperature for 5 days. The reaction was concentrated. The residue was dissolved in EA (500 mL), washed with 10% Na$_2$CO$_3$ (250 mL×2), water (250 mL) and brine (250 mL), dried over Na$_2$SO$_4$, filtered and concentrated to afford product as a yellow solid (20.8 g, 96%).

Step 2: Synthesis of methyl 4-(bromomethyl)-3-chlorobenzoate. Followed Step 1 in the synthesis of Intermediate E using methyl 3-chloro-4-methylbenzoate to give product (10 g, 78%). MS (ESI): m/z 263.0 [M+1]$^+$.

Step 3: Synthesis of methyl 3-chloro-4-(2-methoxy-2-oxoethyl)benzoate. To a solution of methyl 4-(bromomethyl)-3-chlorobenzoate (10 g, 37.95 mmol) in MeOH (300 mL) was added TEA (4.2 mL, 30.36 mmol) and Pd(dppf)Cl$_2$ (2.8 g, 3.8 mmol). The reaction was heated under 0.4 MPa CO pressure at 60° C. for 3 h, filtered and concentrated. The residue was purified by Combi-Flash (120 g silica gel, start PE/EA=10:0 to 5:1 by gradient, 60 mL/min, 60 min, 3.6 L total solvent volume) to afford product as a white solid (2.7 g, 29%). MS (ESI): m/z 243.0 [M+1]$^+$.

Step 4: Synthesis of 2-(2-chloro-4-(methoxycarbonyl)phenyl)acetic acid. Followed procedure described in conversion of compound A-4 to compound A-5 in Method 1 of Synthesis of Intermediate A-1a.

Step 5: Synthesis of methyl 3-chloro-4-(2-(2,4-dihydroxyphenyl)-2-oxoethyl)benzoate (Intermediate F). Followed procedure described in Method 3 (see Intermediate A-2a), using 2-(2-chloro-4-(methoxycarbonyl)phenyl)acetic acid. $^1$H NMR (DMSO-d$_6$, 500 MHz, TMS): δ 12.09 (s, 1H), 10.72 (brs, 1H), 7.97~7.88 (m, 3H), 7.57 (d, J=8.0 Hz, 1H), 6.44 (dd, J=2.5, 8.5 Hz, 1H), 6.30 (d, J=2.0 Hz, 1H), 4.62 (s, 2H), 3.87 (s, 3H); MS (ESI): m/z 321.1 [M+1]$^+$.

Synthesis of Intermediate G: methyl 4-(2-(2,4-dihydroxy-5-methoxyphenyl)-2-oxoethyl)benzoate.

Step 1: Synthesis of 4-formyl-2-methoxyphenyl acetate. To a solution of of 4-hydroxy-3-methoxybenzaldehyde (10 g, 66 mmol) in 30 mL of THF was added Ac$_2$O (8 g, 80 mmol) and TEA (20 g, 198 mmol). The reaction was stirred at room temperature overnight. The volatiles were evaporated to afford 15 g of product as an oil, which was used for next step without further purification.

Step 2: Synthesis of 4-(formyloxy)-2-methoxyphenyl acetate. To a solution of 4-formyl-2-methoxyphenyl acetate (15 g, 77 mmol) in CH$_2$Cl$_2$ (100 mL) was added m-CPBA (31 g, 154 mmol). The solution was refluxed at 50° C. for 2.5 h. The solution was washed with saturated Na$_2$SO$_3$ solution (50 mL), saturated Na$_2$CO$_3$ solution (50 mL) and brine (50 mL), dried over Na$_2$SO$_4$, filtrated and concentrated in vacuo to afford 16 g of crude product as a white solid, which was used for next step without further purification.

Step 3: Synthesis of 4-methoxybenzene-1,3-diol. To a solution of 4-(formyloxy)-2-methoxyphenyl acetate (16 g, 76 mmol) in THF (50 mL)/H$_2$O (50 mL) was added LiOH (7.7 g, 184.2 mmol). The reaction was stirred at room temperature overnight. The volatiles were removed under reduced pressure. The residue was extracted with EA (50 mL×3). The organic phase was washed with brine (50 mL), dried over Na$_2$SO$_4$, filtrated and concentrated in vacuo to give black oil, which was purified by silica gel column (PE:EA=3:1) to afford 4.8 g of product (40%) as a brown solid.

Step 4: Synthesis of methyl 4-(2-(2,4-dihydroxy-5-methoxyphenyl)-2-oxoethyl)benzoate (Intermediate G). Followed procedure described in Method 3 (see Intermediate A), using 4-methoxybenzene-1,3-diol (where reaction was heated at 60° C. overnight). MS (ESI): m/z 317.0 [M+1]$^+$.

Synthesis of Intermediate H: methyl 2-chloro-4-(2-(2,4-dihydroxyphenyl)-2-oxoethyl)benzoate.

Step 1: Synthesis of 1-bromo-4-(bromomethyl)-2-chlorobenzene. Followed Step 1 of Intermediate E using 1-bromo-2-chloro-4-methylbenzene.

Step 2: Synthesis of methyl 2-chloro-4-(2-methoxy-2-oxoethyl)benzoate. Followed Step 2 of Intermediate E. MS (ESI): m/z 243.0 $[M+1]^+$.

Step 3: Synthesis of 2-(3-chloro-4-(methoxycarbonyl)phenyl)acetic acid. Followed Step 4 of Intermediate F. MS (ESI): m/z 229.0 $[M+1]^+$.

Step 4: Synthesis of methyl 2-chloro-4-(2-(2,4-dihydroxyphenyl)-2-oxoethyl)benzoate (Intermediate H). Followed Step 5 of Intermediate F. MS (ESI): m/z 321.7 $[M+1]^+$.

Synthesis of Intermediate I: methyl 4-(2-(2,4-dihydroxyphenyl)-2-oxoethyl)-3-methoxybenzoate.

Step 1: Synthesis of methyl 3-methoxy-4-methylbenzoate, starting with 3-methoxy-4-methylbenzoic acid (see step 1 of Intermediate F). MS (ESI): m/z 181.1 $[M+1]^+$.

Step 2: Synthesis of methyl 4-(bromomethyl)-3-methoxybenzoate (see step 2 of Intermediate F). MS (ESI): m/z 259.1 $[M+1]^+$.

Step 3: Synthesis of methyl 3-methoxy-4-(2-methoxy-2-oxoethyl)benzoate (see step 3 of Intermediate F). MS (ESI): m/z 239.1 $[M+1]^+$.

Step 4: Synthesis of 2-(2-methoxy-4-(methoxycarbonyl)phenyl)acetic acid (see step 4 of Intermediate F). MS (ESI): m/z 225.1 $[M+1]^+$.

Step 5: Synthesis of methyl 4-(2-(2,4-dihydroxyphenyl)-2-oxoethyl)-3-methoxybenzoate (see step 5 of Intermediate F). $^1$H NMR (DMSO-$d_6$, 500 MHz, TMS): δ 12.33 (s, 1H), 10.68 (s, 1H), 7.93 (d, J=9.0 Hz, 1H), 7.55 (dd, J=1.0, 7.0 Hz, 1H), 7.48 (d, J=1.5 Hz, 1H), 7.34 (d, J=8.0 Hz, 1H), 6.41 (dd, J=2.0, 9.0 Hz, 1H), 6.27 (d, J=2.5 Hz, 1H), 4.36 (s, 2H), 3.86 (s, 3H), 3.79 (s, 3H); MS (ESI): m/z 317.1 $[M+1]^+$.

Synthesis of Intermediate J: methyl 4-(2-(5-bromo-2-hydroxy-4-methoxyphenyl)-2-oxoethyl)benzoate.

Step 1: Synthesis of methyl 4-(2-(5-bromo-2,4-dimethoxyphenyl)-2-oxoethyl)benzoate. Followed Step 2 of Method 2 (see Intermediate A) using B-2 and 1-bromo-2,4-dimethoxybenzene. MS (ESI): m/z 395.0 $[M+1]^+$.

Step 2: Synthesis of methyl 4-(2-(5-bromo-2-hydroxy-4-methoxyphenyl)-2-oxoethyl)benzoate (Intermediate J). To a solution of methyl 4-(2-(5-bromo-2,4-dimethoxyphenyl)-2-oxoethyl)benzoate (1.1 g, 2.8 mmol) in DCM (100 mL) was added $AlCl_3$ (7.4 g, 56 mmol) and the mixture was stirred at room temperature for 1 h. Then the mixture was poured into ice-water (100 mL), extracted with DCM (20 mL×4). The organic phase was washed with brine (30 mL), dried with $Na_2SO_4$, filtered and the filtrate was concentrated in vacuo to give brown oil, which was purified by prep-TLC (PE/EA=3/1) to afford Intermediate J (750 mg, 71%) as a light yellow solid. MS (ESI): m/z 379.0 $[M+1]^+$.

Example 24

GSNOR Assays

Various compounds were tested in vitro for their ability to inhibit GSNOR activity. GSNOR expression and purification is described in *Biochemistry* 2000, 39, 10720-10729.

GSNOR Fermentation: Pre-cultures were grown from stabs of a GSNOR glycerol stock in 2XYT media containing 100 ug/ml ampicillin after an overnight incubation at 37° C. Cells were then added to fresh 2XYT (4 L) containing ampicillin and grown to an OD ($A_{600}$) of 0.6-0.9 at 37° C. before induction. GSNOR expression was induced with 0.1% arabinose in an overnight incubation at 20° C.

GSNOR Purification: *E. coli* cell paste was lysed by nitrogen cavitation and the clarified lysate purified by Ni affinity chromatography on an AKTA FPLC (Amersham Pharmacia). The column was eluted in 20 mM Tris pH 8.0/250 mM NaCl with a 0-500 mM imidazole gradient. Eluted GSNOR fractions containing the Smt-GSNOR fusion were digested overnight with Ulp-1 at 4° C. to remove the affinity tag then re-run on the Ni column under the same conditions. GSNOR was recovered in the flowthrough fraction and for crystallography is further purified by Q-Sepharose and Heparin flowthrough chromatography in 20 mM Tris pH 8.0, 1 mM DTT, 10 uM $ZnSO_4$.

GSNOR Assay: GSNO and Enzyme/NADH Solutions are made up fresh each day. The Solutions are filtered and allowed to warm to room temperature. GSNO Solution: 100 mM NaPO4 (pH 7.4), 0.480 mM GSNO. 396 µL of GSNO Solution is added to a cuvette followed by 8 µL of test compound in DMSO (or DMSO only for full reaction control) and mixed with the pipette tip. Compounds to be tested are made up at a stock concentration of 10 mM in 100% DMSO. 2 fold serial dilutions are done in 100% DMSO. 8 µL of each dilution are added to an assay so that the final concentration of DMSO in the assay is 1%. The concentrations of compounds tested range from 100 to 0.003 µM. Enzyme/NADH Solution: 100 mM NaPO4 (pH 7.4), 0.600 mM NADH, 1.0 µg/mL GSNO Reductase. 396 µL of the Enzyme/NADH Solution is added to the cuvette to start the reaction. The cuvette is placed in the Cary 3E UV/Visible Spectrophotometer and the change in 340 nm absorbance/min at 25° C. is recorded for 3 minutes. The assays are done in triplicate for each compound concentration. IC50's for each compound are calculated using the standard curve analysis in the Enzyme Kinetics Module of SigmaPlot.

Final assay conditions: 100 mM NaPO4, pH 7.4, 0.240 mM GSNO, 0.300 mM NADH, 0.5 µg/mL GSNO Reductase and 1% DMSO. Final volume: 800 µL/cuvette.

GSNOR Inhibitor Activity: GSNOR inhibitor activity was determined and $IC_{50}$ values were obtained for the compounds described in Examples 1-21. GSNOR inhibitor compounds Examples 1-21 had an $IC_{50}$ of about <5 µM. GSNOR inhibitor compounds Examples 1, 2, 3, 5, 6, 10, 13, 14, 15, 16, 18, 19, 20 had an $IC_{50}$ of about less than 0.5 µM. GSNOR inhibitor compounds Examples 1, 10, 14, 15, 16, 18, and 20 had an $IC_{50}$ of about less than 0.1 µM.

Example 25

Mouse Pharmacokinetic (PK) Study

Experimental Model

The mouse is used to determine the pharmacokinetics of GSNOR inhibitors. This species is widely used to assess the bioavailability of compounds by administering both oral (PO) and intravenous (IV) test articles. Efficacy of the GSNOR inhibitors can be compared by assessing plasma exposure in male BALB/c mice either via IV or PO administration at the times of peak activity.

Materials and Methods

IV Administration of GSNOR Inhibitors

The GSNOR inhibitor Compound 10 was reconstituted in a phosphate buffered saline (PBS)/10% Solutol (HS 15) clear solution resulting in a concentration of 0.2 mg/mL and administered to mice (2 mg/kg) as a single IV dose. Animals were dosed via the lateral tail vein. Blood samples were collected at designated time points (0.083, 0.25, 0.5, 1, 2, 4, 8, 16, 24 hours) by cardiac puncture under isoflurane anesthesia (up to 1 mL blood per animal). The blood was collected into tubes containing Li-Heparin. The blood samples were kept on ice until centrifugation within approximately 30 minutes of collection. The plasma was transferred into labeled polypropylene tubes and frozen at −70° C. until analyzed by LC/MS/MS.

PO Administration of GSNOR Inhibitors

The GSNOR inhibitor Compound 10 was reconstituted in 40% Propylene Glycol/40% Propylene Carbonate/20% of a 5% Sucrose clear solution resulting in a concentration of 2 mg/mL and administered to mice (10 mg/kg) as a single oral dose via gavage. Blood samples were collected at 0.25, 0.5, 1, 2, 4, 8, 12, 16, 20 and 24 hours post dose by cardiac puncture under isoflurane anesthesia. The blood was collected in tubes containing Li-Heparin. The blood samples were kept on ice until centrifugation within approximately 30 minutes of collection. The plasma was transferred into labeled polypropylene tubes and frozen at −70° C. until analyzed by LC/MS/MS.

LC/MS/MS Analysis

Plasma samples at each timepoint were analyzed using a LC-MS/MS with a lower limit of quantification (LLOQ) of 1 ng/mL. Plasma was analyzed to determine the amount of the GSNOR inhibitor in each sample and regression curves were generated for each GSNOR inhibitor in the relevant matrixes.

WinNonlin analysis was used for calculating PK parameters for both the IV and PO administrations:

PK parameters for IV portion—$AUC_{last}$; $AUC_{INF}$; T1/2; Cl; Vss; $C_{max}$; MRT PK parameters for PO portion—$AUC_{last}$; $AUC_{INF}$; T1/2; $C_{max}$; Cl, MRT.

In addition to the above PK parameters, calculation of bioavailability (% F) was performed.

Results

IV administration: Plasma levels of GSNOR inhibitor Compound 10 were measured up to 24 hours post-dose.

Oral administration: Plasma levels of Compound 10 were measured up to 24 hours post dose, based on area under the curve a mean oral bioavailability was determined. Compound 10 had an oral bioavailability of greater than 17 percent.

Example 26

Efficacy of GSNORi in Experimental Asthma

Experimental Asthma Model:

A mouse model of ovalbumin (OVA)-induced asthma is used to screen GSNOR inhibitors for efficacy against methacholine (MCh)-induced bronchoconstriction/airway hyper-reactivity. This is a widely used and well characterized model that presents with an acute, allergic asthma phenotype with similarities to human asthma. Efficacy of GSNOR inhibitors are assessed using a prophylactic protocol in which GSNOR inhibitors are administered prior to challenge with MCh. Bronchoconstriction in response to challenge with increasing doses of MCh is assessed using whole body plethysmography ($P_{enh}$; Buxco). The amount of eosinophil infiltrate into the bronchoaveolar lavage fluid (BALF) is also determined as a measure of lung inflammation. The effect of GSNOR inhibitors are compared to vehicles and to Combivent (inhaled; IH) as the positive control.

Materials and Methods

Allergen Sensitization and Challenge Protocol

OVA (500 μg/ml) in PBS is mixed with equal volumes of 10% (w/v) aluminum potassium sulfate in distilled water and incubated for 60 min. at room temperature after adjustment to pH 6.5 using 10 N NaOH. After centrifugation at 750×g for 5 min, the OVA/alum pellet is resuspended to the original volume in distilled water. Mice receive an intraperitoneal (IP) injection of 100 μg OVA (0.2 mL of 500 μg/mL in normal saline) complexed with alum on day 0. Mice are anesthetized by IP injection of a 0.2-mL mixture of ketamine and xylazine (0.44 and 6.3 mg/mL, respectively) in normal saline and are placed on a board in the supine position. Two hundred fifty micrograms (100 μl of a 2.5 mg/ml) of OVA (on day 8) and 125 μg (50 μl of 2.5 mg/ml) OVA (on days 15, 18, and 21) are placed on the back of the tongue of each animal.

Pulmonary Function Testing (Penh)

In vivo airway responsiveness to methacholine is measured 24 h after the last OVA challenge in conscious, freely moving, spontaneously breathing mice with whole body plethysmography using a Buxco chamber (Wilmington, N.C.). Mice are challenged with aerosolized saline or increasing doses of methacholine (5, 20 and 50 mg/mL) generated by an ultrasonic nebulizer for 2 min. The degree of bronchoconstriction is expressed as enhanced pause ($P_{enh}$), a calculated dimensionless value, which correlates with the measurement of airway resistance, impedance, and intrapleural pressure in the same mouse. $P_{enh}$ readings are taken and averaged for 4 min. after each nebulization challenge. $P_{enh}$ is calculated as follows: $P_{enh}=[(T_e/T_r-1)\times(PEF/PIF)]$, where $T_e$ is expiration time, $T_r$ is relaxation time, PEF is peak expiratory flow, and PIF is peak inspiratory flow×0.67 coefficient. The time for the box pressure to change from a maximum to a user-defined percentage of the maximum represents the relaxation time. The $T_r$ measurement begins at the maximum box pressure and ends at 40%.

Eosinophil Infiltrate in BALF

After measurement of airway hyper-reactivity, the mice are exsanguinated by cardiac puncture, and then BALF is collected from either both lungs or from the right lung after tying off the left lung at the mainstem bronchus. Total BALF cells are counted from a 0.05 mL aliquot, and the remaining fluid is centrifuged at 200×g for 10 min at 4° C. Cell pellets are resuspended in saline containing 10% BSA with smears made on glass slides. Eosinophils are stained for 5 min with 0.05% aqueous eosin and 5% acetone in distilled water, rinsed with distilled water, and counterstained with 0.07% methylene blue.

GSNOR Inhibitors and Controls

GSNOR inhibitors are reconstituted in phosphate buffered saline (PBS), pH 7.4, at concentrations ranging from 0.00005 to 3 mg/mL. GSNOR inhibitors are administered to mice (10 mL/kg) as a single dose either intravenously (IV) or orally via gavage. Dosing is performed from 30 min. to 24 h prior to MCh challenge. Effect of GSNOR inhibitors are compared to PBS vehicle dosed in the same manner.

Combivent is used as the positive control in all studies. Combivent (Boehringer Ingelheim) is administered to the lung using the inhaler device supplied with the product, but adapted for administration to mice, using a pipet tip. Combivent is administered 48 h, 24 h, and 1 h prior to MCh challenge. Each puff (or dose) of Combivent provides a dose of 18 μg ipatropium bromide (IpBr) and 103 μg albuterol sulfate or approximately 0.9 mg/kg IpBr and 5 mg/kg albuterol.

Statistical Analyses

Area under the curve values for $P_{enh}$ across baseline, saline, and increasing doses of MCh challenge are calculated using GraphPad Prism 5.0 (San Diego, Calif.) and expressed as a percent of the respective (IV or orally administered) vehicle control. Statistical differences among treatment groups and the respective vehicle control group within each study are calculated using one-way ANOVA, Dunnetts (JMP 8.0, SAS Institute, Cary, N.C.). A p value of <0.05 among the treatment groups and the respective vehicle control group is considered significantly different.

Example 27

Efficacy of GSNOR Inhibitors in Experimental Inflammatory Bowel Disease (IBD)

Experimental Model

An acute model of dextran sodium sulfate (DSS)-induced IBD in mice is used to explore efficacy of GSNOR inhibitors against this disease. Acute DSS-induced IBD is a widely used and well characterized model that induces pathological changes in the colon similar to those observed in the human disease. In this model and in human disease, epithelial cells within the crypts of the colon are disrupted, leading to dysfunction of the epithelial barrier and the ensuing tissue inflammation, edema, and ulceration. GSNOR inhibitor therapy may benefit IBD by restoring s-nitrosogluthathione (GSNO) levels, and thus prevent or reverse the epithelial barrier dysfunction.

Experimental IBD is induced by administration of DSS in the drinking water over several days. GSNOR inhibitors are administered daily via intravenous (IV) dosing. Effect of treatment is assessed via endoscopy and histopathology using a five point scale ranging from a score=0 (normal tissue) to a score=4 (ulcerative tissue damage and marked pathological changes). The effect of GSNOR inhibitors is compared to vehicle treated controls. The corticosteroid, prednisolone, is used as the positive control in this study and is administered daily via oral dosing. Naïve mice are also assessed as a normal tissue control.

Materials and Methods

Experimental IBD is induced by administration of 3% DSS in the drinking water on study days 0 to 5. GSNOR inhibitors are reconstituted to concentrations of 0.2 and 2 mg/ml in phosphate buffered saline (PBS), pH 7.4. Mice are treated daily via IV administration of 0.1 ml GSNOR inhibitor solution per mouse for doses of 1 and 10 mg/kg/day. GSNOR inhibitor dosing is started 2 days prior to the DSS administration and continued through the last day of the study (days −2 to 7). PBS is used as the vehicle control and is administered in the same manner as the GSNOR inhibitor. The corticosteroid, prednisolone, is used as the positive control for the study, and is administered orally at a dose of 3 mg/kg/day on each day (study days −2 to 7).

The effect of drug treatment is assessed on day 7 via endoscopy and histopathology. Mice are first anesthetized with inhaled isoflurane and subjected to endoscopy using a veterinary endoscope (Karl Storz Veterinary Endoscopy America, Inc., Goleta, Calif.). Each mouse is scored for mucosal injury using the endoscopy scoring criteria. An endoscopy score of 0 is normal, 1 is loss of vascularity, 2 is loss of vascularity and friability, 3 is friability and erosions, and 4 is ulcerations and bleeding. Following endoscopy, mice are euthanized via asphyxiation with inhaled carbon dioxide. Colon sections are then formalin-fixed, paraffin-embedded, sectioned, and stained with hematoxylin-eosin. Colon sections are examined via light microscopy and scored in a blinded fashion by a board certified veterinary pathologist with particular expertise in GI pathology. Pathological changes to the epithelium, connective tissue, and submucosa are scored based on inflammation, edema, and necrosis, and a score of 0 is normal, 1 is minimal, 2 is mild, 3 is moderate, and 4 is marked.

Example 28

Efficacy of GSNOR Inhibitors in Experimental Chronic Obstructive Pulmonary Disease (COPD)

Experimental COPD Model

An acute model of elastase-induced COPD in mice is used to explore efficacy of GSNOR inhibitors against this disease. Elastase-induced COPD is a widely used and well characterized model that induces pathological changes in the lung similar to those observed in the human disease. In this model and in human disease, airway obstruction, pulmonary inflammation, and airspace enlargement are evident. GSNOR inhibitor therapy may benefit COPD through the bronchodilatory and anti-inflammatory actions of these compounds.

Experimental COPD is induced by administration of the elastases, papain and porcine pancreatic elastase (PPE), into the lung over several days. GSNOR inhibitors are administered daily via oral dosing. Efficacy is determined by assessing the ability of GSNOR inhibitors to attenuate bronchoconstriction in response to methacholine (MCh) aerosol challenge, decrease pulmonary inflammation, and reduce airspace enlargement in the aveoli. The effect of GSNOR inhibitors are compared to vehicle treated controls. A combination of daily oral SP CXC receptor 2/receptor 1 (SP CXCR2/1) antagonist, which blocks recruitment of neutrophils and monocytes, and inhaled Flovent (fluticasone; corticosteroid), is used as the positive control in this study.

Materials and Methods

Experimental COPD is induced by administration of 80 µg papain and 20 U/mg PPE per mouse per day via intratracheal (IT) instillation on study days 0 to 7. GSNOR inhibitor is reconstituted to concentrations of 0.01, 0.1, and 1 mg/ml in phosphate buffered saline (PBS), pH 7.4. Mice are treated daily via oral administration (gavage) of 0.1 ml GSNORi solution per mouse for doses of 0.1, 1, and 10 mg/kg/day. PBS is used as the vehicle control and is administered via daily oral dosing. The small molecule antagonist SP CXCR2/R1 (Schering-Plough/Merck), which blocks receptors to cytokine chemoattractants for neutrophil and monocyte recruitment, is used in combination with the corticosteroid, Flovent (Glaxo), as the positive control for the study. SP CXCR2/R1 is dosed orally at 50 mg/kg/day. Flovent is dosed via inhalation at 220 µg/mouse/day. One group of mice is treated with GSNOR inhibitor, vehicle control, or positive control for 7 days (study days 8 to 14), while a second group of mice is treated with GSNOR inhibitor, vehicle control, or positive control for 14 days (study days 8 to 21).

The effect of drug treatment is assessed 7 and 14 days post-treatment by measuring attenuation of methacholine-induced bronchoconstriction (bronchodilatory effect), attenuation of pulmonary inflammation, and reduction of airspace enlargement in the alveoli (14 day post-treatment only).

Bronchodilatory Effect

In vivo airway responsiveness to methacholine is measured in conscious, freely moving, spontaneously breathing mice with whole body plethysmography using a Buxco chamber (Wilmington, N.C.). Mice are challenged with aerosolized saline or increasing doses of methacholine (5, 20, and 50 mg/ml) generated by an ultrasonic nebulizer for 2 min. The degree of bronchoconstriction is expressed as enhanced pause (Penh), a calculated dimensionless value, which correlated with the measurement of airway resistance, impedance, and intrapleural pressure in the same mouse. Penh readings are taken and averaged for 4 min after each nebulization challenge. Penh is calculated as follows: Penh= $[(T_e/T_r-1) \times (PEF/PIF)]$, where $T_e$ is expiration time, $T_r$ is relaxation time, PEF is peak expiratory flow, and PIF is peak inspiratory flow×0.67 coefficient. The time for the box pressure to change from a maximum to a user-defined percentage of the maximum represented the relaxation time. The $T_r$ measurement began at the maximum box pressure and ended at 40%.

Anti-Inflammatory Effect

After measurement of airway hyper-reactivity, the mice are exsanguination by cardiac puncture, and then bronchoalveolar lavage fluid (BALF) is collected from the right lung after tying off the left lung at the mainstem bronchus. Total BALF cells are counted, and the remaining fluid is centrifuged at 200×g for 10 min. at 4° C. Cell pellets are resuspended in saline containing 10% bovine serum albumin (BSA) and smears are made on glass slides using cytospin. Cells are stained with Diff-Quik for white blood cell (WBC) differential counts via light microscopy. Epithelial cells are counted and subtracted from the total number of cells. The proportions of eosinophils, macrophages, neutrophils, and lymphocytes are counted using standard morphological criteria and expressed as a percentage of the total number of white blood cells (WBCs).

The ability of treatment to reduce levels of neutrophil and monocyte chemoattractants in the BALF are also assessed as additional parameters of anti-inflammatory effect. KC (keratinocyte chemoattractant), also known as GROα (growth-related oncogene alpha), and JE (MCP-1, monocyte chemoattractant protein), chemokines for neutrophil and monocyte recruitment, respectively, are measured using immunoassay.

Reduction of Airspace Enlargement

Both lungs are inflated under constant positive pressure at 25 cm water pressure with 10% buffered formaldehyde and then perfused-fixed. The fixed lungs are embedded in paraffin, stained with hematoxylin and eosin, and examined via light microscopy. Airspace enlargement is quantified morphologically by calculating the mean linear intercept (Lm) and average equivalent diameter of alveoli (D2).

* * *

It will be apparent to those skilled in the art that various modifications and variations can be made in the methods and compositions of the present invention without departing from the spirit or scope of the invention.

The invention claimed is:

1. A method of alleviating the symptoms or complications of pulmonary disorders which comprises administering to a patient in need thereof a therapeutically effective amount of a compound of Formula (I) or a pharmaceutically acceptable salt thereof

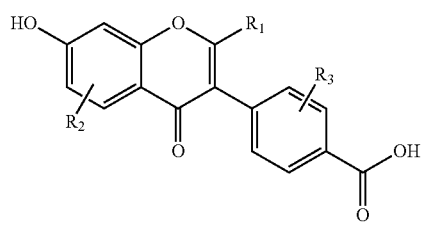

wherein $R_1$ is selected from the group consisting of $CF_3$, $CF_2H$, $CF_2CH_3$, $CF_2CH_2CH_3$, isopropyl, isobutyl, cyclopentyl, $CH_2OCH_3$, $SCH_3$, benzyl, thiophen-2-yl, and thiophen-3-yl;

$R_2$ is selected from H, F, Cl, methoxy, and cyano; and $R_3$ is selected from H, F, Cl, and methoxy.

2. The method of claim 1 wherein $R_1$ is selected from the group consisting of $CF_3$, $CF_2H$, and $CF_2CH_3$; and $R_2$ is hydrogen.

3. The method of claim 1 wherein $R_1$ is selected from the group consisting of $CF_3$, isopropyl, and isobutyl; and $R_2$ and $R_3$ are both hydrogen.

4. The method of claim 1 wherein $R_1$ is selected from the group consisting of $CF_3$, isopropyl, isobutyl, $CF_2H$, $CF_2CH_3$, and $CF_2CH_2CH_3$; and $R_2$ and $R_3$ are both hydrogen.

5. The method of claim 1 wherein the compound of Formula (I) or a pharmaceutically acceptable salt thereof is selected from the group consisting of
4-(2-(difluoromethyl)-7-hydroxy-4-oxo-4H-chromen-3-yl)benzoic acid;
4-(7-hydroxy-2-(methoxymethyl)-4-oxo-4H-chromen-3-yl)benzoic acid;
4-(7-hydroxy-2-isopropyl-4-oxo-4H-chromen-3-yl)benzoic acid;
4-(2-cyclopentyl-7-hydroxy-4-oxo-4H-chromen-3-yl)benzoic acid;
4-(2-benzyl-7-hydroxy-4-oxo-4H-chromen-3-yl)benzoic acid;
4-(7-hydroxy-4-oxo-2-(thiophen-2-yl)-4H-chromen-3-yl)benzoic acid;
4-(7-hydroxy-4-oxo-2-(thiophen-3-yl)-4H-chromen-3-yl)benzoic acid;
4-(7-hydroxy-2-isobutyl-4-oxo-4H-chromen-3-yl)benzoic acid;
4-(7-hydroxy-4-oxo-2-(trifluoromethyl)-4H-chromen-3-yl)benzoic acid;
4-(7-hydroxy-2-(methylthio)-4-oxo-4H-chromen-3-yl)benzoic acid;
4-(6-chloro-7-hydroxy-4-oxo-2-(trifluoromethyl)-4H-chromen-3-yl)benzoic acid;
4-(6-fluoro-7-hydroxy-4-oxo-2-(trifluoromethyl)-4H-chromen-3-yl)benzoic acid;
2-fluoro-4-(7-hydroxy-4-oxo-2-(trifluoromethyl)-4H-chromen-3-yl)benzoic acid;
3-chloro-4-(7-hydroxy-4-oxo-2-(trifluoromethyl)-4H-chromen-3-yl)benzoic acid;
4-(2-(1,1-difluoroethyl)-7-hydroxy-4-oxo-4H-chromen-3-yl)benzoic acid;
4-(7-hydroxy-6-methoxy-4-oxo-2-(trifluoromethyl)-4H-chromen-3-yl)benzoic acid;
2-chloro-4-(7-hydroxy-4-oxo-2-(trifluoromethyl)-4H-chromen-3-yl)benzoic acid;
4-(2-(1,1-difluoropropyl)-7-hydroxy-4-oxo-4H-chromen-3-yl)benzoic acid;
4-(7-hydroxy-4-oxo-2-(trifluoromethyl)-4H-chromen-3-yl)-3-methoxybenzoic acid; and
4-(6-cyano-7-hydroxy-4-oxo-2-(trifluoromethyl)-4H-chromen-3-yl)benzoic acid.

6. The method of claim 1 comprising administering to a patient in need thereof a therapeutically effective amount of a compound of Formula (I) or a pharmaceutically acceptable salt thereof together with a pharmaceutically accepted carrier or excipient.

7. A method of alleviating the symptoms or complications of inflammatory disorders which comprises administering to a patient in need thereof a therapeutically effective amount of a compound of Formula (I) or a pharmaceutically acceptable salt thereof

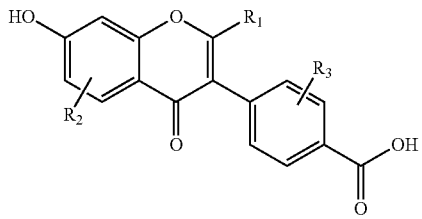

wherein
$R_1$ is selected from the group consisting of $CF_3$, $CF_2H$, $CF_2CH_3$, $CF_2CH_2CH_3$, isopropyl, isobutyl, cyclopentyl, $CH_2OCH_3$, $SCH_3$, benzyl, thiophen-2-yl, and thiophen-3-yl;
$R_2$ is selected from H, F, Cl, methoxy, and cyano; and
$R_3$ is selected from H, F, Cl, and methoxy.

8. The method of claim 7 wherein $R_1$ is selected from the group consisting of $CF_3$, $CF_2H$, and $CF_2CH_3$; and $R_2$ is hydrogen.

9. The method of claim 7 wherein $R_1$ is selected from the group consisting of $CF_3$, isopropyl, and isobutyl; and $R_2$ and $R_3$ are both hydrogen.

10. The method of claim 7 wherein $R_1$ is selected from the group consisting of $CF_3$, isopropyl, isobutyl, $CF_2H$, $CF_2CH_3$, and $CF_2CH_2CH_3$; and $R_2$ and $R_3$ are both hydrogen.

11. The method of claim 7 wherein the compound of Formula (I) or a pharmaceutically acceptable salt thereof is selected from the group consisting of
- 4-(2-(difluoromethyl)-7-hydroxy-4-oxo-4H-chromen-3-yl)benzoic acid;
- 4-(7-hydroxy-2-(methoxymethyl)-4-oxo-4H-chromen-3-yl)benzoic acid;
- 4-(7-hydroxy-2-isopropyl-4-oxo-4H-chromen-3-yl)benzoic acid;
- 4-(2-cyclopentyl-7-hydroxy-4-oxo-4H-chromen-3-yl)benzoic acid;
- 4-(2-benzyl-7-hydroxy-4-oxo-4H-chromen-3-yl)benzoic acid;
- 4-(7-hydroxy-4-oxo-2-(thiophen-2-yl)-4H-chromen-3-yl)benzoic acid;
- 4-(7-hydroxy-4-oxo-2-(thiophen-3-yl)-4H-chromen-3-yl)benzoic acid;
- 4-(7-hydroxy-2-isobutyl-4-oxo-4H-chromen-3-yl)benzoic acid;
- 4-(7-hydroxy-4-oxo-2-(trifluoromethyl)-4H-chromen-3-yl)benzoic acid;
- 4-(7-hydroxy-2-(methylthio)-4-oxo-4H-chromen-3-yl)benzoic acid;
- 4-(6-chloro-7-hydroxy-4-oxo-2-(trifluoromethyl)-4H-chromen-3-yl)benzoic acid;
- 4-(6-fluoro-7-hydroxy-4-oxo-2-(trifluoromethyl)-4H-chromen-3-yl)benzoic acid;
- 2-fluoro-4-(7-hydroxy-4-oxo-2-(trifluoromethyl)-4H-chromen-3-yl)benzoic acid;
- 3-chloro-4-(7-hydroxy-4-oxo-2-(trifluoromethyl)-4H-chromen-3-yl)benzoic acid;
- 4-(2-(1,1-difluoroethyl)-7-hydroxy-4-oxo-4H-chromen-3-yl)benzoic acid;
- 4-(7-hydroxy-6-methoxy-4-oxo-2-(trifluoromethyl)-4H-chromen-3-yl)benzoic acid;
- 2-chloro-4-(7-hydroxy-4-oxo-2-(trifluoromethyl)-4H-chromen-3-yl)benzoic acid;
- 4-(2-(1,1-difluoropropyl)-7-hydroxy-4-oxo-4H-chromen-3-yl)benzoic acid;
- 4-(7-hydroxy-4-oxo-2-(trifluoromethyl)-4H-chromen-3-yl)-3-methoxybenzoic acid; and
- 4-(6-cyano-7-hydroxy-4-oxo-2-(trifluoromethyl)-4H-chromen-3-yl)benzoic acid.

12. The method of claim 7 comprising administering to a patient in need thereof a therapeutically effective amount of a compound of Formula (I) or a pharmaceutically acceptable salt thereof together with a pharmaceutically accepted carrier or excipient.

\* \* \* \* \*